United States Patent
Zangen et al.

(10) Patent No.: US 7,407,478 B2
(45) Date of Patent: Aug. 5, 2008

(54) COIL FOR MAGNETIC STIMULATION

(75) Inventors: Abraham Zangen, Jerusalem (IL); Roy A. Wise, Baltimore, MD (US); Mark Hallett, Bethesda, MD (US); Pedro Cavaleiro Miranda, Lisbon (PT); Yiftach Roth, Ramat-Gan (IL)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 829 days.

(21) Appl. No.: 10/399,559

(22) PCT Filed: Oct. 19, 2001

(86) PCT No.: PCT/US01/50737

§ 371 (c)(1),
(2), (4) Date: Oct. 9, 2003

(87) PCT Pub. No.: WO02/32504

PCT Pub. Date: Apr. 25, 2002

(65) Prior Publication Data

US 2004/0078056 A1 Apr. 22, 2004

Related U.S. Application Data

(60) Provisional application No. 60/242,297, filed on Oct. 20, 2000.

(51) Int. Cl.
*A61N 1/00* (2006.01)
(52) U.S. Cl. .......................... 600/13; 600/15
(58) Field of Classification Search ............... 600/9–15; 607/45, 58
See application file for complete search history.

(56) References Cited

U.S. PATENT DOCUMENTS 4,994,015 A  2/1991  Cadwell (Continued)

FOREIGN PATENT DOCUMENTS

EP  0595227 A1  5/1994

(Continued)

OTHER PUBLICATIONS

Breiter et al., "Acute Effects of Cocaine on Human Brain Activity and Emotion," *Neuron* 19:591-611 (1997).

(Continued)

*Primary Examiner*—Samuel G Gilbert
(74) *Attorney, Agent, or Firm*—Klarquist Sparkman, LLP

(57) ABSTRACT

A magnetic stimulator, which may be used as a transcranial magnetic stimulation (TMS) device, and a method for its use are disclosed. The stimulator comprises a frame and an electrically conductive coil having a partially toroidal or ovate base and an outwardly projecting extension portion. The frame may be a flexible or malleable material and may be non-conductive. The electrically conductive coil may comprise one or more windings of electrically conductive material (such as a wire) coupled to the frame. The coil is electrically connected to a power supply. The device may be placed adjacent to or in contact with the body of a subject, such as on the head of a subject. The device may be used on humans for treating certain physiological conditions, such as cardiovascular or neurophysiological conditions, or for studying the physiology of the body. This device is useful in studying or treating neurophysiological conditions associated with the deep regions of the brain, such as drug addiction and depression.

71 Claims, 11 Drawing Sheets

U.S. PATENT DOCUMENTS

| | | | |
|---|---|---|---|
| 5,000,178 A * | 3/1991 | Griffith | 607/2 |
| 5,078,674 A | 1/1992 | Cadwell | |
| 5,116,304 A * | 5/1992 | Cadwell | 600/13 |
| 5,169,380 A * | 12/1992 | Brennan | 600/26 |
| 5,707,334 A | 1/1998 | Young | |
| 5,738,625 A | 4/1998 | Gluck | |
| 5,769,778 A | 6/1998 | Abrams et al. | |
| 6,048,302 A | 4/2000 | Markoll | |
| 6,066,084 A | 5/2000 | Edrich et al. | |
| 6,086,525 A | 7/2000 | Davey et al. | |
| 6,402,678 B1 * | 6/2002 | Fischell et al. | 600/13 |
| 6,447,440 B1 * | 9/2002 | Markoll | 600/13 |

FOREIGN PATENT DOCUMENTS

| | | |
|---|---|---|
| JP | 5-237197 | 9/1993 |
| JP | 2892181 | 2/1999 |
| WO | WO 98/06342 | 2/1998 |

OTHER PUBLICATIONS

Klein et al., "Therapeutic Efficacy of Right Prefrontal Slow Repetitive Transcranial Magnetic Stimulation in Major Depression—A Double-blind Controlled Study," *Arch. Gen. Psychiat.* 56:315-320 (1999).

Paus et al., "Transcranial Magnetic Stimulation during Positron Emission Tomography: A New Method for Studying Connectivity of the Human Cerebral Cortex," *J. Neurosci.* 17:3178-3184 (1997).

Bishop et al., "Intracranial Self-Stimulation in Man," *Science* 140:394-396 (1963).

Cadwell, "Optimizing Magnetic Stimulator Design," *Magnetic Motor Stimulation: Principles and Clinical Experience* 43:238-248 (1991).

Zimmermann et al., "Slinky coils for neuromagnetic stimulation," *Electroencephalography and clinical Neurophysiology* 101:145-152 (1996).

Cohen et al., "Effects of coil design on delivery of focal magnetic stimulation. Technical considerations," *Electroencephalography and clinical Neurophysiology* 75:350-357 (1990).

Ruohonen et al., "Focusing and targeting of magnetic brain stimulation using multiple coils," *Medical & Biological Engineering & Computing* pp. 297-301 (May 1998).

Yunokuchi et al., "Developing a More Focal Magnetic Stimulator. Part II: Fabricating Coils and Measuring Induced Current Distributions," *J. of Clinical Neurophysiology* 8:112-120 (1991).

George et al., "Transcranial Magnetic Stimulation," *Arch. Gen. Psychiatry*, vol. 56, pp. 300-311 (1999).

Hallett, "Transcranial magnetic stimulation and the human brain," *Nature*, vol. 406, pp. 147-150 (Jul. 2000).

Branston et al., "Analysis of the distribution of currents induced by a changing magnetic field in a volume conductor," *Phys. Med. Biol.*, vol. 36, No. 2, pp. 161-168 (1991).

Branston et al., "Magnetic stimulation of a volume conductor produces a negligible component of induced current perpendicular to the surface," *King's College London Meeting*, Dec. 15-16, 1989, 1 pp.

Brasil-Neto et al., "Optimal Focal Transcranial Magnetic Activation of the Human Motor Cortex: Effects of Coil Orientation, Shape of the Induced Current Pulse, and Stimulus Intensity," *Journal of Clinical Neurophysiology*, vol. 9, pp. 132-136 (1992).

Cohen et al., "Developing a More Focal Magnetic Stimulator. Part I: Some Basic Principles," *Journal of Clinical Neurophysiology*, vol. 8, pp. 102-111 (1991).

Eaton, "Electric field induced in a spherical volume conductor from arbitrary coils: application to magnetic stimulation and MEG," *Medical & Biological Engineering & Computing*, vol. 30, pp. 433-440 (1992).

Kraus et al., "The Use of a Cap-Shaped Coil for Transcranial Magnetic Stimulation of the Motor Cortex," *Journal of Clinical Neurophysiology*, vol. 10, pp. 353-362 (1993).

Maccabee et al., "Spatial distribution of the electric field induced in volume by round and figure '8' magnetic coils: relevance to activation of sensory nerve fibers," *Electroencephalography and clinical Neurophysiology*, vol. 76, pp. 131-141 (1990).

Ren et al., "A Novel Electric Design for Electromagnetic Stimulation—The Slinky Coil," IEEE Transactions on Biomedical Engineering, vol. 42, No. 9, pp. 918-925 (Sep. 1995).

Roth et al., "A Coil Design for Transcranial Magnetic Stimulation of Deep Brain Regions," *Journal of Clinical Neurophysiology*, vol. 19, pp. 361-370 (2002).

Tofts, "The distribution of induced currents in magnetic stimulation of the nervous system," *Phys. Med. Biol.*, vol. 35, No. 8, pp. 1119-1128 (1990).

Tofts et al., "The measurement of electric field, and the influence of surface charge, in magnetic stimulation," *Electroencephalography and clinical Neurophysiology*, vol. 81, pp. 238-239 (1991).

* cited by examiner

COIL FOR MAGNETIC STIMULATION

CROSS REFERENCE TO RELATED APPLICATIONS

This is the U.S. National Stage of International Application No. PCT/US01/50737, filed Oct. 19, 2001, which was published in English under PCT Article 21(2) and which claims the benefit of U.S. Provisional Application No. 60/242,297, filed Oct. 20, 2000. Both applications are incorporated herein in their entirety.

FIELD

This invention relates to coils for magnetic stimulation, particularly transcranial magnetic stimulation, and more particularly to transcranial magnetic stimulation capable of stimulating deep regions of the brain.

BACKGROUND

Electromagnets are capable of inducing electric fields in most biological tissues. Transcranial magnetic stimulation (TMS) is widely used as a research tool to study aspects of the human brain, including motor function, vision, language, and brain disorders. Additionally, therapeutic uses of magnetic stimulation devices, particularly in psychiatry, currently are being investigated.

Magnetic stimulation of biological tissue may be accomplished by passing a brief, high-current electric pulse through a coil of electrically conductive material, such as a wire positioned adjacent tissue to be stimulated. A magnetic field is produced by the electric pulse with lines of flux passing perpendicularly to the plane of the magnetic coil. This magnetic field, in turn, can induce an electric field in a conductive medium. An animal brain is a conductive medium and in TMS, the induced electric field stimulates the neurons of the brain. However, an electromagnetic coil may be placed over other parts of the body to stimulate other electrically conductive tissues, such as muscle.

Functional magnetic coils may be produced in a variety of shapes including circles, FIG. 8's, squares, petals, spirals, and "slinky" coils. See, e.g. Caldwell, J., *Optimizing Magnetic Stimulator Design, Magnetic Motor Stimulation: Basic Principles and Clinical Experience*, 1991, 238-48 (ed. Levy, W. J., et al.); Zimmermann, K. P., and Simpson, R. K., *Electroencephal. Clin. Neurophysiol.*, 101:145-52 (1996); U.S. Pat. No. 6,066,084 (Edrich et al.). The coils may include features other than a coil of a transducing material. For example, U.S. Pat. No. 6,086,525 (Davey et al.) and WO 98/06342 (Epstein et al.) disclose magnetic stimulators made from coil windings around a core of ferromagnetic material, preferably vanadium permendur. However, such coils can be quite heavy and expensive to manufacture.

TMS using known coils has been shown to be able to stimulate the regions of the brain close to the surface of the skull, but magnetic fields produced by these known coils generally do not penetrate deeply into the brain, unless the intensity of the magnetic field is greatly increased. However, increasing the strength or intensity of the magnetic field carries a risk of causing physiological damage and seizures.

The deep regions of the brain include the nucleus accumbens, a portion of the brain that plays a major role in rewarding circuits and is known to be activated in response to doses of cocaine. Additionally, neuronal fibers connecting the medial, prefrontal, or cingulate cortex with the nucleus accumbens have a role in reward and motivation, and activation of the nucleus accumbens also may cause hedonic effects.

Known coils used for TMS (e.g., a figure eight coil) affect the cortical regions of the brain, primarily the cortical region under the center of the coil. However, the intensities of the electric fields produced by these known coils decrease very rapidly with increasing distance from the coil. Therefore, stimulating deep regions of the brain using known coils would require either invading the skull (and often the brain) with the coil, or using a high intensity electric field. Invasive techniques often cause the subject or patient to experience pain or discomfort, and would usually be avoided by the patient. High intensity electric fields may cause epileptic seizures or other neurological problems. Moreover, high intensity electric fields may cause generalized effects throughout a subject's brain, rather than stimulating a specific deep region of the brain, and may cause other harmful side effects. Additionally, the maximum field intensity can be limited by known coil designs.

Therefore, a need exists for a magnetic coil capable of stimulating the deep regions of the brain when placed outside the skull during non-invasive TMS.

SUMMARY

The present invention relates to a coil for magnetic stimulation. The coil may be placed externally of a body part of a subject and, when so placed, is operable to induce electric currents within the body of that subject. The magnetic coil may be used as a transcranial magnetic stimulation (TMS) device and is capable of stimulating the deep regions of the brain, such as the nucleus accumbens.

The device comprises a frame and an electrically conductive coil, which may have a partially toroidal or ovate base and an outwardly projecting extension portion. The partially toroidal or ovate base has a concave first side that is usually directed toward the body of the subject. The extension portion extends from the second side of the base (i.e., away from the concave first side). The frame may be a flexible or malleable material, and the electrically conductive coil may comprise one or more windings of electrically conductive material (such as a wire) coupled to the frame. The coil is electrically connected to a power supply.

Particular embodiments use a power supply capable of producing a rate of current change in the range of about 10,000 amperes per 100 microseconds or higher to produce an electric field within the biological tissue, such as the brain, in a range from about 10 to about 100 volts per meter or higher. The coil may be activated by one or more pulses of electric current, with a pulse generally lasting about 1000 microseconds.

The device may be placed adjacent to or in contact with the body of a subject (such as an animal). In particular embodiments, the device is placed on top of the head of a human subject. However, the apparatus could be placed anywhere on the body of a subject and used to magnetically stimulate a tissue or multiple tissues of that subject's body, such as by inducing electric fields within such tissues. If the device is placed externally to the skull of the subject, the device may be placed in various orientations around the skull.

The device has a base portion with a first end, a second end, a length axis, and a width axis. In some embodiments, the configuration of the base comprises an arch along each axis. This arch configuration (along both the length and width axes) is generally complementary to the external shape of the body part with which the device is used, and comprises a generally toroidal or ovate shape.

The overall length of the base (as measured along the length axis) can be adapted to a particular subject or class of subjects, depending on the size of the subject and location on the body where the device will be placed. A device with an arch length along the length axis of the base of about 26 centimeters has been found suitable for use with most adult humans, if the device is to be placed externally to the skull of the subject. Additionally, the overall width of the partially toroidal or ovate base (as measured along the width axis) can be adapted to a particular subject or class of subjects, depending on the size of the subject and location on the body where the device will be placed. For adult human subjects, the device may have an arch length along the width axis in the range of about 5 centimeters, if the device is to be placed externally of the skull of the subject.

The extension portion provides a return path for the flow of electricity through the partially toroidal or ovate base. In some embodiments, the extension has a minimal number of components extending radially of the base in order to reduce opposition to or interference with the magnetic fields produced by the coil portions in the base. A particular embodiment accomplishes this objective by using a triangular, or upwardly converging, extension. However, the extension may form shapes other than triangular—such as arcuate, or hemispherical—so long as the extension provides reduced radial components and reduces interference with the magnetic fields produced by the coil in the base.

In alternative embodiments, the extension comprises a collection of individual return paths in the form of elongated elements projecting radically outwardly from the base portion. For example, the extension may include a number of return paths (corresponding to individual wires) arranged in a fan-like pattern. In such embodiments, the individual return paths optionally may be offset in a forward or rearward direction.

The coil comprises one or more windings of an electrically conductive material, such as a metal band or wires that function as electrical transducers. In some embodiments, the windings are associated with the frame. For example, wire may be run alongside of, mounted to, wound around, or placed inside the frame, so long as the frame is not electrically conductive. In other embodiments, the frame itself is the coil. The device coil also may comprise other electrical components, such as resistors and capacitors.

The magnetic stimulator also may include a cushion placed adjacent to the first side of the base, which faces the subject. The device also may comprise some nonconductive material, such as plastic or rubber, that encases the frame and coil, and may employ a frame made from some flexible or malleable material. Particular embodiments use a flexible or malleable base in order to allow the user to better align the coil and allow some portions of the coil to lie tangential to the body surface of the subject.

The device can be used in a variety of ways and on any part of subject's body. Any conductive tissue, including (but not limited to) nervous tissue and muscle tissue, may be stimulated by the device.

The device may be used on humans for treating certain physiological conditions, such as neurophysiological conditions, or for studying the physiology of the body. For example, the device may be used to study or treat neurophysiological conditions associated with the deep regions of the brain, such as drug addiction and depression.

One embodiment of the method for using the device comprises identifying a subject suffering a neurophysiological condition; providing an electrically conductive coil as described above (i.e., having a partially toroidal or ovate base with a concave first side to be directed toward a body part of the subject); placing the coil external to the subject's skull; electrically connecting a power supply to the coil; and activating the coil to stimulate the deep region of the subject's brain. The device may be used in combination with brain imaging, such as magnetic resonance imaging (MRI) or positron emission tomography (PET), to study the effect of deep brain stimulation on other regions of the brain. Many embodiments comprise non-invasively stimulating a subject's brain.

In some embodiments, a train of electromagnetic pulses is administered to the subject. The pulse train may comprise an appropriate number of individual pulses administered over a certain period of time. The number and frequency of pulses may vary. Certain embodiments use a frequency range of about 20 to about 30 Hz. The train of pulses may be administered during a certain period of time, such as from about 20 to about 30 seconds. Plural trains of magnetic pulses also may be administered at a single session. If the subject is suffering a specific condition, multiple treatment sessions may be conducted until clinical improvement occurs.

DETAILED DESCRIPTION

As used herein, the singular forms of "a," "an," and "the," refer to both the singular as well as plural, unless the context clearly indicates otherwise. For example, the term "a coil" includes singular or plural coils and can be considered equivalent to the phrase "at least one coil."

As used herein, the term "comprises" means "includes."

The present invention relates to a coil for magnetic stimulation that, when placed externally of a body part of a subject, is operable to induce electric currents within the body of that subject. In particular embodiments, the magnetic coil may be used for transcranial magnetic stimulation (TMS). If placed outside the skull of a subject, the device is capable of stimulating the brain of the subject, including the deep regions of the brain, such as the nucleus accumbens. Methods for using this device include treating neurophysiological conditions, such as clinical or non-clinical depression, substance abuse, and drug addiction.

Figure 1:
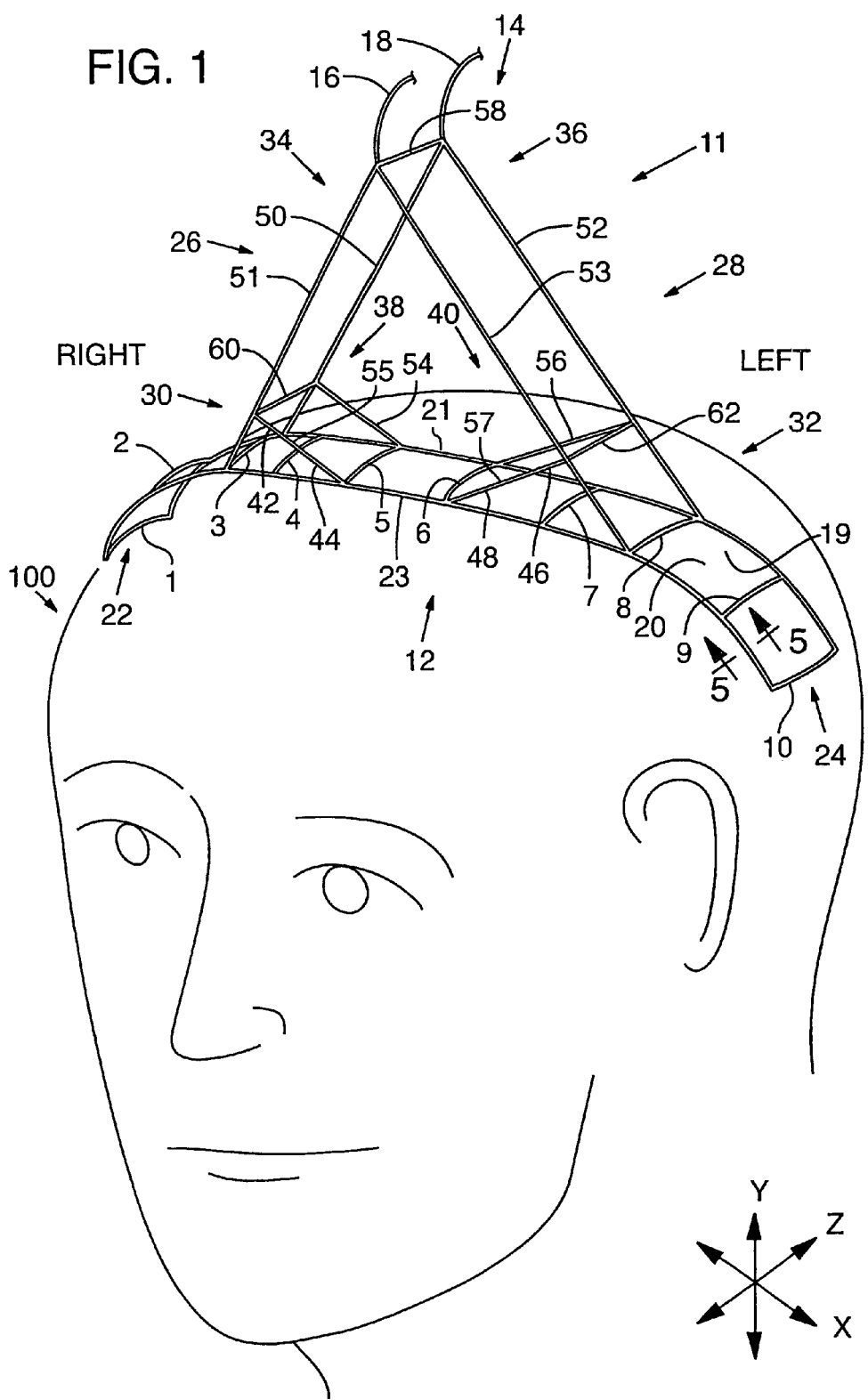
FIG. 1 illustrates a perspective view of one embodiment of the device placed on the head of a human.

FIG. 1 shows one embodiment of the device. The device 11 comprises a frame and an electrically conductive coil having a partially toroidal or ovate base 12 and an outwardly projecting extension portion 14. In some embodiments, the frame itself is the electrically conductive coil, such as a frame composed of electrically conductive material. In other embodiments, however, the frame is a flexible or malleable material, which may be configured to a desired shape for a specific application, and the electrically conductive coil comprises one or more windings of electrically conductive material associated with the frame, such as being run alongside of, mounted to, wound around, or placed inside the frame.

The coil is electrically connected to a power supply (not shown), such as by electrical leads 16, 18 in FIG. 1. Other embodiments may employ a similar connection to a power supply via similar electrical leads.

The coil may be composed of any electrically conductive material, such as metal. Particular embodiments have coils comprising wire made of copper, aluminum, or other electrically conductive material. The power supply may be any appropriate commercially available power supply, such as the power supplies available for use with other magnetic coils. Examples of such power supplies include those sold with various models of magnetic stimulators produced by Medtronic, Inc. of Minneapolis, Minn., USA (e.g., MagPro, MagLite Compact), or power supplies sold with various models of magnetic stimulators produced by Magstim Company US, LLC, of New York, N.Y., USA (e.g., Magstim Model 200, Magstim Model 220, Magstim Model 250, BiStim, Magstim Rapid, Magstim QuadroPulse).

Particular embodiments use a power supply capable of producing a rate of current change in the range of about 10,000 ampere per 100 microseconds or higher, depending on coil inductance, to produce an electric field in a range from about 10 to about several hundred volts per meter. The coil may be activated by one or more pulses of electric current, with each pulse lasting up to about 2000 microseconds. In particular embodiments, the pulse length is about 1000 microseconds in duration.

For stimulating nerve tissue, such as brain tissue, maximal current and the rise of time of the current at the beginning of the pulse largely determine the pulse length. These parameters largely depend on the power supply used to generate the electrical pulse and the inductance of the coil. In some embodiments, one turn of the coil has an inductance of about 10 microhenri. A commercially available power supply (described above) can generate an electrical pulse in the coil having a pulse length of about 1000 microseconds. However, the pulse length may be altered by changing the capacitance and/or resistance in the circuit, and/or the inductance or resistance of the coil.

The partially toroidal or ovate base 12 has a concave first, or outer, side 19, which is directed toward the body part of the subject, and a second, or inner, side 20 opposite first side 19. The extension portion 14 extends outwardly from this second side 20 and away from the base.

The device may be placed adjacent to or in contact with the body of a subject. FIG. 1 illustrates placement of the device 11 on the top of the head 100 of a human subject. However, the apparatus could be placed anywhere on the body of a subject and used to magnetically stimulate tissues of that subject's body, such as by inducing electric fields within such tissues. Additionally, the subject may be any animal, such as a mammal including a human.

If the device is placed externally of the skull of the subject, the device may be placed in various orientations around the skull. For example, FIG. 1 shows the device 11 placed on top of the skull. The device 11 could be placed at the back of the skull, across the subject's forehead, or elsewhere on the skull. However, the device 11 effectively induces electric fields within the body of a subject when the device 11 is placed with the concave side 19 of the base 12 facing the body of the subject.

The device 11 pictured in FIG. 1 has a partially toroidal or ovate base 12 with a first end 22 and a second end 24. A line extending between these two ends 22, 24 defines a length axis along the length of the base 12. The base 12 has a substantially arcuate, semi-circular or semi-ovate shape along its length axis, as further illustrated in FIG. 3. The base 12 also has a width axis extending perpendicular to its length axis and this width axis has a substantially arcuate, semicircular or semi-ovate shape as further illustrated in FIG. 4. Thus, the base 12 pictured in FIG. 1 comprises an arch extending along its length axis and an arch extending along its width axis.

In the illustrated embodiment, the arch configurations along both the length and width axes are complementary to the external shape of the body part with which the device is to be used. In the illustrated embodiment, the device conforms to the side-to-side and front-to-back arch shape of a subject's skull.

The extent of the base 12 can be described in terms of degrees of rotation or distance in length. The length axis of the base 12 extends less than about 360 degrees, such as extending less than about 270 degrees. For example, the length axis of the base 12 of the device illustrated in FIGS. 1 and 3 extends about 180 degrees in rotation. The overall length of the base (as measured along the length axis) can be adapted to a particular subject or class of subjects, depending on the size of the subject and where on the body the device will be placed. Some embodiments of the device have an arch length along the length axis of the base in a range of from about 10 to about 50 centimeters. For adult human subjects, the device may have an arch length along the length axis of the base in a range of from about 20 to about 30 centimeters. A device with an arch length along the length axis of the base of about 26 centimeters has been found sufficient for use with most adult humans, if the device is to be placed externally to the skull of the subject.

Similar to the length axis, the width axis of the base 12 extends less than 360 degrees, such as extending less than about 270 degrees, less than about 180 degrees, or even less than about 90 degrees. For example, the width axis of the base 12 of the device illustrated in FIGS. 1 and 4 extends about 45 degrees in rotation.

Additionally, the overall width of the base (as measured along the width axis) can be adapted to a particular subject or class of subjects, depending on the size of the subject and where on the body the device will be placed. Some embodiments of the device have an arch length along the width axis in a range of from about 2 to about 15 centimeters. For adult human subjects, the device may have an arch length along the width axis in the range of about 5 centimeters, if the device is to be placed externally to the skull of the subject.

The extent of the base—whether measured in degrees of rotation about, or distance in length along, either the length axis or width axis—can be adapted to fit a particular subject or method of use, so as long as the base remains substantially toroidal or ovate. For example, the concave first side 19 of the base 12 can be configured to be complementary to the cranium of a subject.

The extension 14 provides a path for the flow of electricity to and from the base 12. In the embodiment illustrated in FIGS. 1-4, the extension has two components extending radially of the base in order to reduce creation of a surface charge in the subject's tissue, such as a surface charge on the brain of the subject. This surface charge can interfere with and reduce the strength of the electric field produced by the coil portions in the base. The embodiment of FIG. 1 accomplishes this objective by using a triangular, or upwardly converging, extension 14. The extension 14 comprises first and second elongated elements, 26, 28. The elements have a first set of inner ends 30, 32 connected to the base 12 at positions spaced apart along the length axis of the base 12. In FIG. 1, the first elongated element 26 has a first inner end 30 connected to the base 12 adjacent to the first end 22 of the base 12, and the second elongated element 28 has a first inner end 32 connected to the base 12 adjacent to the second end 24 of the base 12. The remainder portions 34, 36 of these elements 26, 28 extend away from the base 12 and converge toward each other.

In the embodiment of FIG. 1, the first and second inner ends 30, 32 are interconnected through a central portion of base 12 to form a triangular shape. This triangular shape is further illustrated by FIG. 3. However, the extension may form shapes other than triangular—such as arcuate or hemispherical—so long as the extension provides reduced radial components and reduces interference with the electric fields produced by the coil in the base 12. For example, the triangular extension portion 14 allows the current flow through electrical conductors in the extension portion 14 to reach the base 12 at an orientation substantially tangential to the body part of the subject, such as the skull of the human pictured in FIGS. 1 and 3. A similar substantially tangential relationship between the extension portion and the body part of the subject may be accomplished by extension portions having other shapes as well.

The extension portion also may comprise a unibody element, rather than separate elements. For example, a device similar to the embodiment illustrated in FIGS. 1 and 3 could be made using a unibody extension element rather than the two separate elongated elements 26, 28. The extension portion also may comprise three or more elements. Additionally, the extension may be centered over the base, or placed off-center relative to the base.

Figure 3:
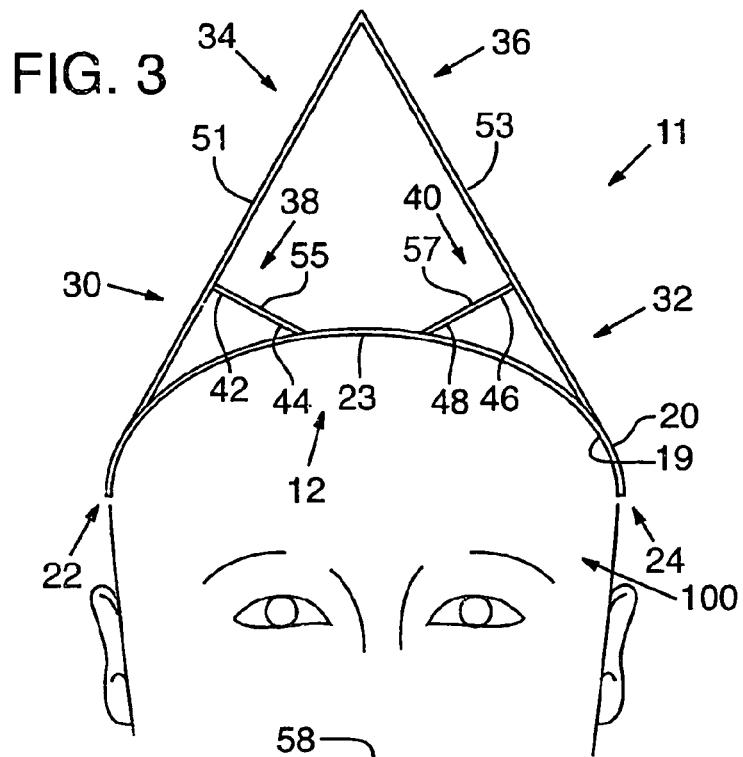
FIG. 3 illustrates a frontal view of the device of FIG. 1.

If a triangular extension portion is used (whether a unibody element or comprised of plural elements), this triangular portion will comprise three interior angles. For example, the extension portion illustrated by FIG. 1 (discussed above) has a first angle formed by the inner end 30 of the first element 26 and the base 12, a second interior angle formed by the inner end 32 of the second element 28 and the base 12, and a third angle formed by the remainder portions 34, 36 of the two elements 26, 28. These three angles may be equivalent or different degrees in measurement. In many embodiments, the angles are all less than about 90 degrees, and in some embodiments, the angles are all less than about 75 degrees. In particular embodiments, the triangular shape approximates an isosceles triangle with the three angles each being about 60 degrees. However, the first and second angles may be less than 60 degrees, since the partially toroidal base will provide some arc. For example, the triangular extension portion 14 illustrated in FIG. 3 has three interior angles, each measuring about 60 degrees. If the third angle of FIG. 3 is 60 degrees, the first and second interior angles would still be less than 60 degrees due to the upward arch of the base 12.

The extension portion also may comprise braces. The braces may provide some structural stability and support to the extension portion, and may provide some alternative pathways for electricity flow through the coil. For example, the extension portion 14 of the device 11 illustrated in FIG. 1 has first and second elongated braces 38, 40, each brace having first ends 42, 46 and second ends 44, 48. The first end 42 of the first brace 38 is coupled adjacent to the inner end 30 of the first elongated element 26, and the second end 44 of the first brace 38 is coupled to the base 12. The first end 46 of the second brace 40 is coupled adjacent to the inner end 32 of the second elongated element 28 and the second end 48 of the second brace 40 is coupled to the base 12. In this particular embodiment, the braces 38, 40 are coupled to the base 12 between each inner end 30, 32 of the elongated elements 26, 28. In this particular embodiment, the braces 38, 40, elongated elements 26, 28, and base 12 also define triangular shapes. However, other embodiments may have braces coupled to different portions of the elongated elements and/or base, or may not include such braces at all.

In the embodiment illustrated in FIG. 1, the base includes a pair of substantially parallel, arcuate, elongate, longitudinally-extending, laterally spaced frame members 21 and 23. These have the arcuate configuration illustrated in FIG. 3. Extending between and interconnecting longitudinal frame members 21 and 23 are ten elongate, arcuate transverse frame members 1, 2, 3, 4, 5, 6, 7, 8, 9, 10. As is seen in FIG. 1, members 1-10 are spaced apart along the lengths of longitudinal frame members 21 and 23 and are coupled at their opposite ends to, and extend generally at right angles to, longitudinal frame members 21 and 23. Arcuate transverse frame members 1, 2, 3, 4, 5, 6, 7, 8, 9, 10 may be spaced apart from each other by any suitable distance, such as from about 1 mm to about 5 cm, depending on the overall length of base 12 and the number of arcuate transverse frame members. The distance between two adjacent arcuate transverse frame members 1, 2, 3, 4, 5, 6, 7, 8, 9, 10 may be the same as or different than the distance between two other arcuate transverse frame members 1, 2, 3, 4, 5, 6, 7, 8, 9, 10. In particular embodiments, arcuate transverse frame members 1, 2, 3, 4, 5, 6, 7, 8, 9, 10 are separated from each other by a distance of about 1 cm.

However, in alternative embodiments, the longitudinally extending laterally spaced frame members, 21 and 23, are not substantially parallel along their entire lengths. This non-parallel orientation may be accomplished by altering the lengths of the transverse elements along the base. For example (and without limitation), the transverse elements near the first end of the base may be shorter than the transverse elements near the second end of the base.

Extension element 26 includes a pair of elongate, substantially parallel, spaced extension frame members 50 and 51. Extension element 28 includes a pair of elongate, substantially parallel, spaced extension frame members 52 and 53. The lower ends of members 51 and 53 are coupled to spaced apart locations on longitudinal frame member 23 and the lower sets of ends of members 50 and 52 are coupled at spaced apart locations to longitudinal frame member 21. Three spacer members 58, 60, and 62 extend between frame members 50, 51, 52, 53 to maintain a selected spacing therebetween.

Brace 38 includes a pair of elongate, laterally spaced elements 54 and 55 which are coupled at their upper ends to frame members 50 and 51, and at their lower ends to longitudinal frame members 21 and 23 respectively. Similarly, brace 40 includes a pair elongate, laterally spaced elements 56 and 57 coupled at their upper sets of ends to extension frame members 52 and 53 and at their lower ends to longitudinal frame members 21 and 23, respectively.

The embodiment illustrated in FIGS. 1-4 includes a minimal number of components extending radially of the base to form extension 14. In alternative embodiments, extension 14 includes a greater number of radially extending components, such as the embodiment illustrated in FIGS. 8-11, described in more detail below.

Figure 2:
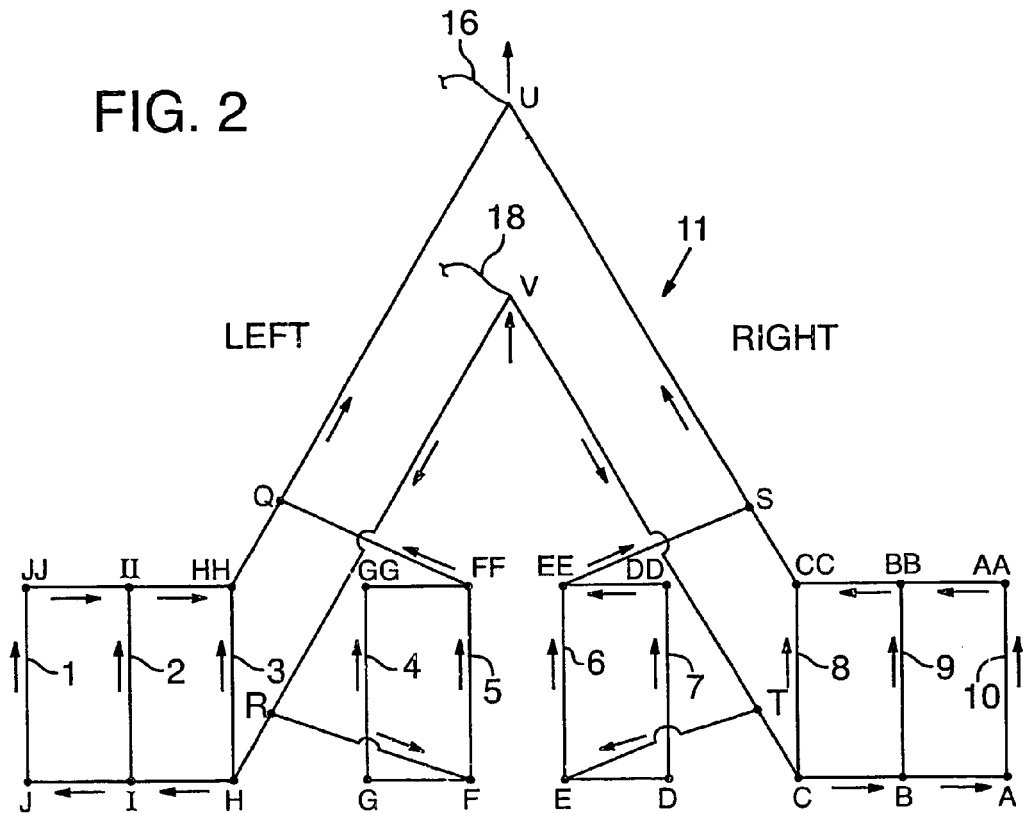
FIG. 2 illustrates an electrical diagram for a magnetic coil embodied in the device shown in FIG. 1.

As stated above, the device comprises a frame and an electrically conductive coil. In some embodiments, the frame itself may function as the coil. However, in other embodiments, the coil comprises a separate structure as part of the device, and may even include multiple coils. FIG. 2, discussed in more detail below, is an electrical circuit diagram for one possible coil configuration for the embodiment illustrated in FIG. 1.

In particular embodiments, the coil comprises one or more windings of an electrically conductive material, such as a metal wire. These windings comprise electrical transducers. In these embodiments, the windings are associated with the frame; for example, wire may be run alongside of, be mounted to, or placed inside of the frame, so long as the wire forming the windings does not contact any electrically conductive portion of the frame. Such a configuration is shown in FIG. 5, which shows a cross section through the base 12 illustrated in FIG. 1.

Figure 5:
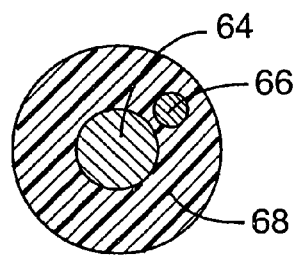
FIG. 5 illustrates an enlarged cross-section through the device shown in FIG. 1, taken at line 5-5.

In FIG. 5, an exemplary frame element 64 and conducting wire 66 are shown surrounded by an insulating material 68, such as plastic or rubber. If the frame is made of an electrically conductive material, the wire 66 would need to be spaced apart from the frame element 64, and may be separated from the frame element 64 by a layer of the insulating material 68. Additionally, a cross section through other parts of the base 12 or extension portion 14 of the embodiment illustrated in FIG. 1 might show plural wires, depending on the placement of windings on the frame. In some embodiments, a winding is associated with an elongated element, a brace element, or both. In particular embodiments, a winding is associated with each elongated element and each brace element.

FIG. 2 is a schematic electrical diagram illustrating conducting wires and current flow in the embodiment illustrated in FIG. 1. In FIG. 2, points labeled A-J and AA-JJ are associated with the base, and points Q-V are associated with the extension portion. Points U and V correspond to the electrical inputs for the current produced by the power supply (not shown). Using the circuit diagram of FIG. 2 as a guide, one can understand how a coil might be constructed for the embodiment of FIG. 1. For example, the device 11 illustrated by FIG. 1 could comprise a coil having ten windings numbered 1-10 extending in the arch width direction of the base along the ten elongate, arcuate transverse frame members 1-10. Table 1 summarizes such a placement of windings.

TABLE 1

| Winding No. | Pathway |
|---|---|
| 1 | V-R-H-I-J-JJ-II-HH-Q-U |
| 2 | V-R-H-I-II-HH-Q-U |
| 3 | V-R-H-HH-Q-U |
| 4 | V-R-F-G-GG-FF-Q-U |
| 5 | V-R-F-FF-Q-U |
| 6 | V-T-E-EE-S-U |
| 7 | V-T-E-D-DD-EE-S-U |
| 8 | V-T-C-CC-S-U |

TABLE 1-continued

| Winding No. | Pathway |
|---|---|
| 9 | V-T-G-B-BB-CC-S-U |
| 10 | V-T-C-B-A-AA-BB-CC-S-U |

Alternative embodiments of the device could comprise a coil with more or less than ten windings, however. Furthermore, the windings could comprise a single wire or plural wires, such as separate wires for each winding. In some embodiments, different windings may have different numbers of wires. In some embodiments, the different windings of the coil are connected in series. However, in alternative embodiments, windings are connected in parallel. Alternatively, the device illustrated by FIGS. 1 and 2 could be produced by a coil comprising a single winding, such as a coil comprising an electrically conductive frame, so long as the coil comprised an appropriate circuit.

The device coil illustrated by the FIG. 2 circuit diagram is made up of transducers. However, the device also may comprise other electrical components, such as resistors, inductors, or capacitors to produce an appropriate circuit, such as the circuit illustrated in FIG. 2. Whether other electrical components are necessary for a particular embodiment will depend on several factors including, (but not limited to): the type of generator used; the frequency, amperage, and voltage of the current passing through the circuit; the resistance of the transducer(s); and the timing of activation of the circuit.

The particular embodiment illustrated by FIGS. 1 and 2 has a coil comprising two major portions: a portion associated with the partially toroidal or ovate base 12, and a portion associated with the extension portion 14. In this embodiment, the length of the portion of the coil comprising the base is oriented substantially parallel to the width axis of the base by associating the coil with several transverse frame elements 1-10. These transverse strips of the coil correspond to sections 1-10 of the circuit diagram in FIG. 2 (i.e., pathways A-AA, B-BB, C-CC . . . H-HH, I-II, and J-JJ). In such an embodiment, a significant portion of the current flowing through the base flows through these strips and, therefore, is oriented substantially along the reference z-axis shown in FIG. 1. Additionally, as further illustrated by FIGS. 3 and 4, the coil portions associated with the base are complementary and tangential to the surface of the subject's skull. In particular embodiments, the total length of the coil associated with the transverse frame elements 1-10 (i.e., substantially parallel to the width axis of the base) exceeds the remaining length of the coil associated with the base (i.e., the remaining length substantially parallel to the length axis of the base). In these embodiments, a majority of the current flowing through the base is oriented substantially along the referenced z-axis shown in FIG. 1.

The device also may comprise a cushion placed adjacent to the first side or underside 19 of the base 12 which faces the subject. A cushion made from suitable material, such as cloth, foam, or rubber, may provide an additional measure of comfort for a subject when the device is used on the subject. Additionally, as illustrated in FIG. 5 the device may also comprise some nonconductive material, such as plastic or rubber, that encases the frame and coil.

The device also may comprise a shield or screen (not shown, for sake of clarity) placed around one or more elements of the extension portion 14. This shield or screen can inhibit or block the magnetic fields produced when electricity runs through the portions of the coil in extension portion 14.

Figure 12:
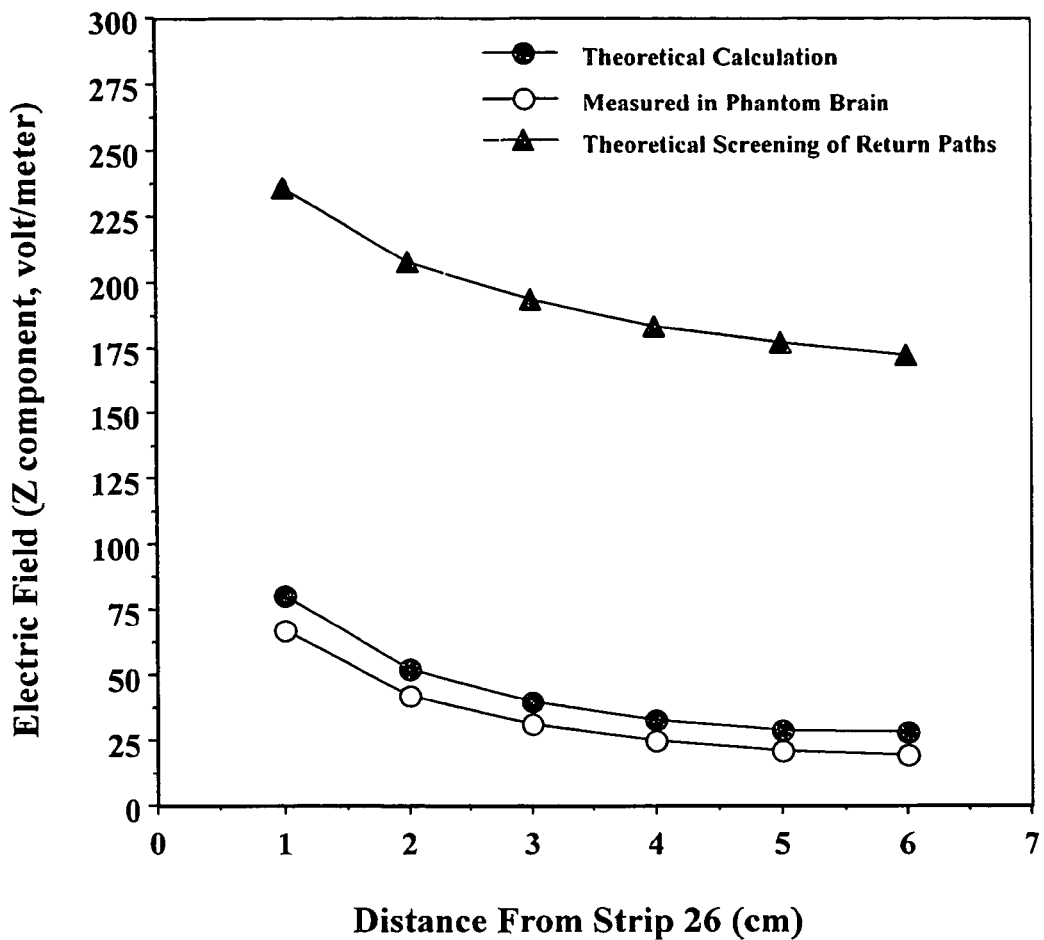
FIG. 12 is a graph comparing theoretical calculations and actual measurements of electric field strength for the embodiment illustrated in FIGS. 8-10.
Figure 13:
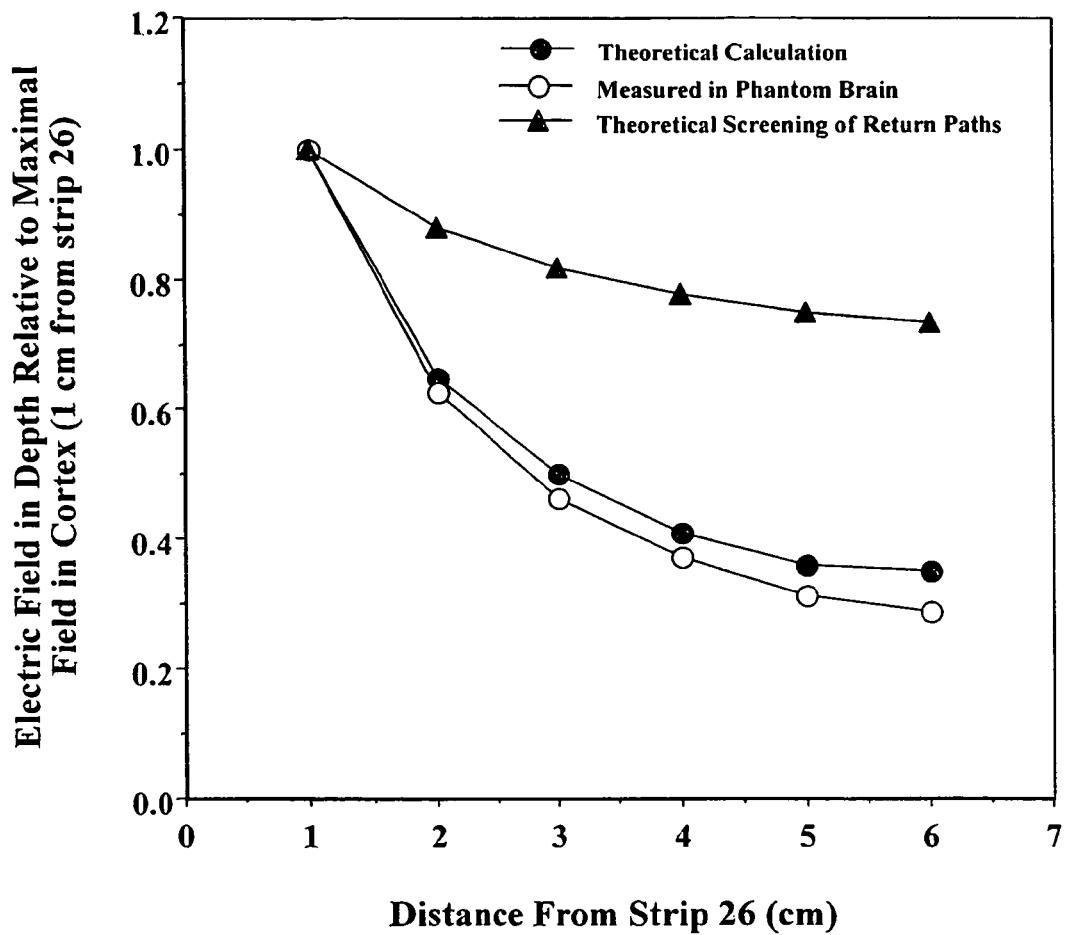
FIG. 13 is a graph comparing theoretical calculations and actual measurements of electric field strength, relative to the maximal field strength in the brain cortex, for the embodiment illustrated in FIGS. 8-10.

Since the magnetic fields produced by the extension can interfere with the magnetic fields produced by the portions of the coil in base 12, screening the magnetic fields produced by extension portion 14 can reduce the interference with the magnetic fields produced by base 12 and, therefore, increase the strength of the electrical fields induced in a conductive medium by the magnetic fields of base 12. As just one, non-limiting example, Example 3 below, and FIGS. 12-13, show the effects of screening the return paths of extension 14. Any suitable screen or shield capable of inhibiting magnetic fields may be used, though in some embodiments, a metal is used as a screen, such as mu metal, which is known to efficiently screen magnetic fields. The screen may be any suitable size or shape, including (but not limited to), sheaths of mu metal surrounding one, some, or all of the elements of extension 14; a flat disc of metal placed intermittently within extension 14 that would inhibit the magnetic and electric fields produced by extension 14 from interfering with those produced by base 12; or an enclosure substantially enclosing extension 14. This shielding diverts the magnetic flux produced by the extension portion to the shielding, thus reducing interference with the fields produced by the base portion.

Figure 8:
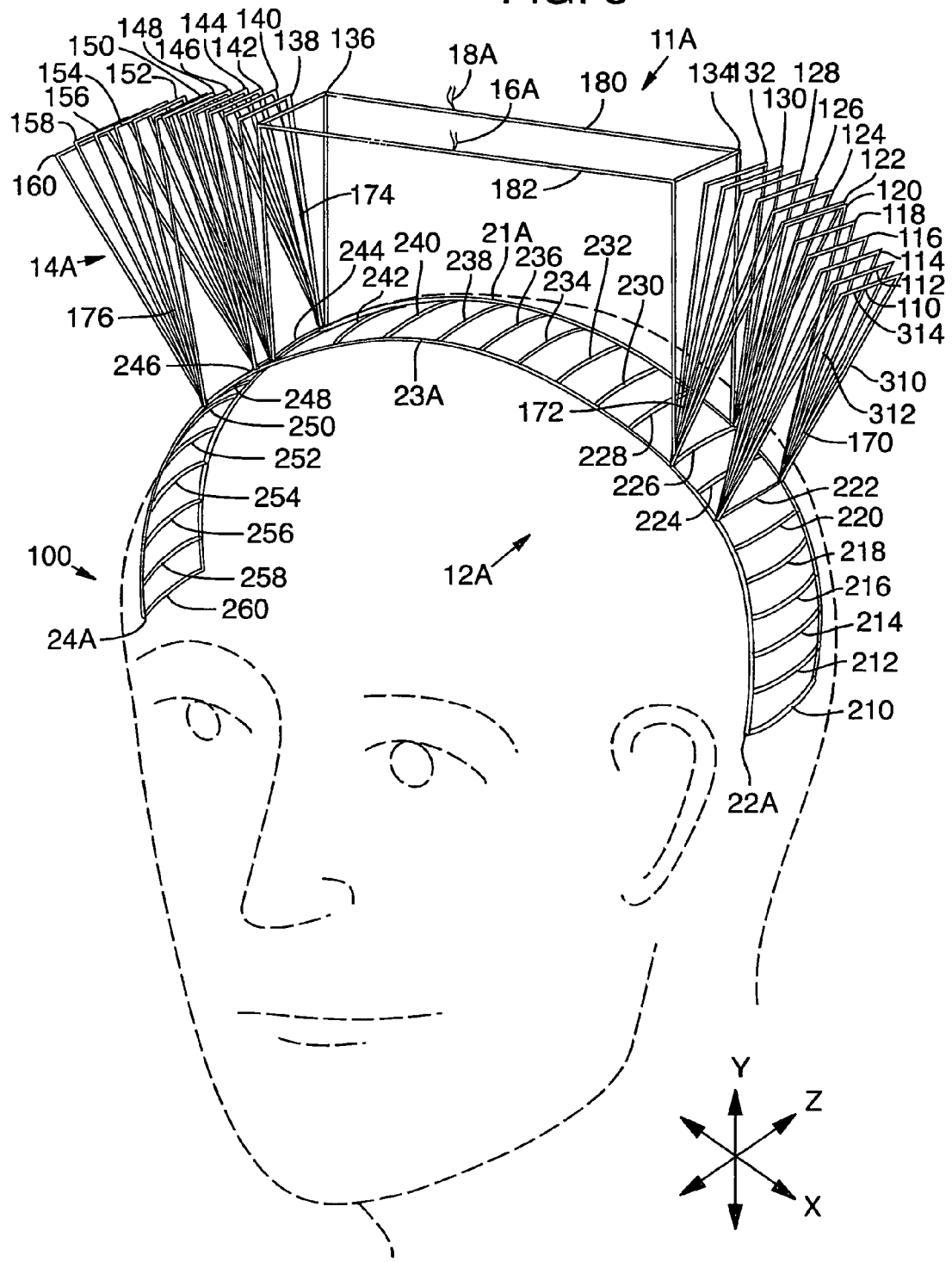
FIG. 8 is a perspective view of a second embodiment of the device placed on the head of a human.
Figure 9:
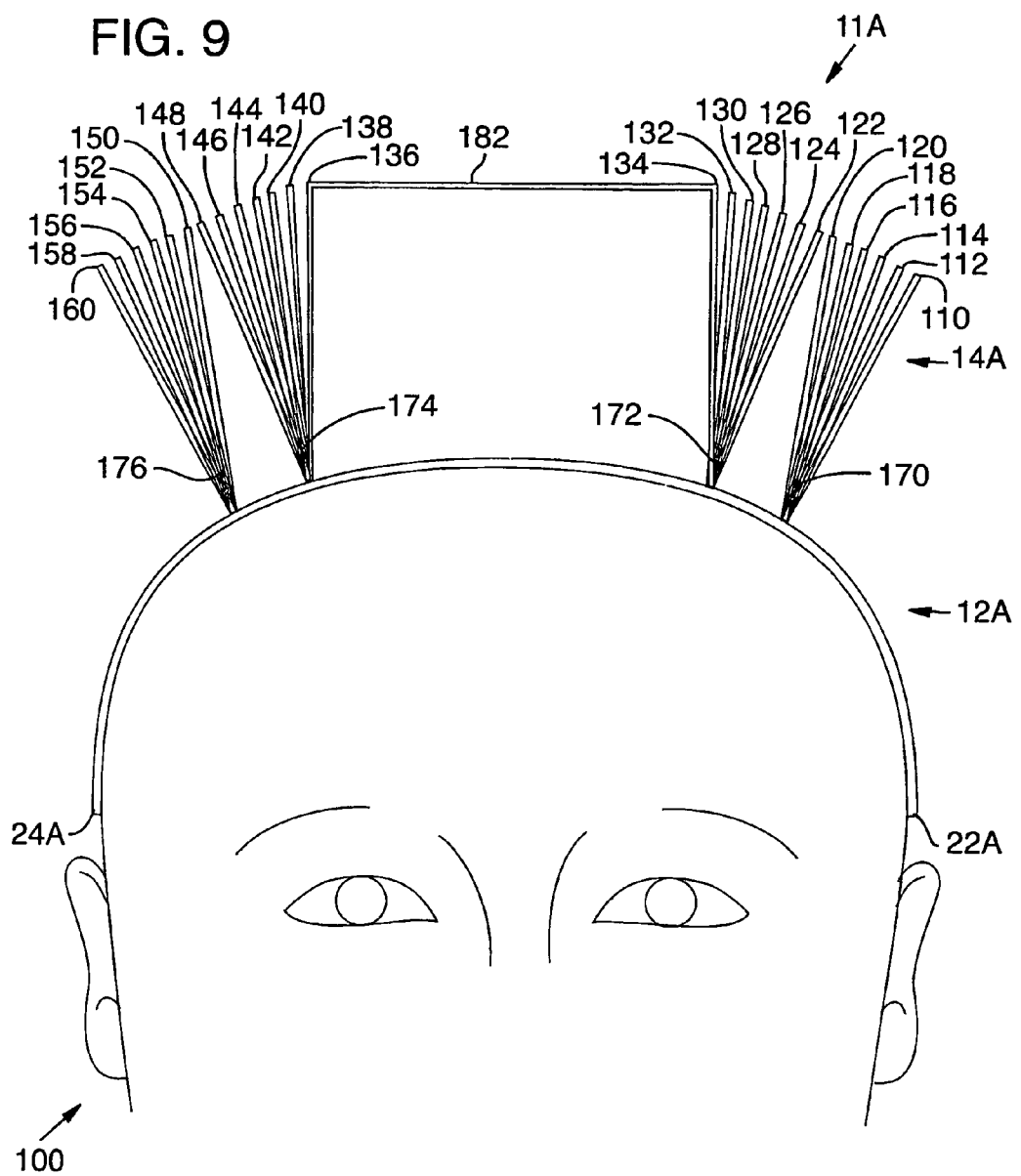
FIG. 9 is a frontal view of the device of FIG. 8.
Figure 10:
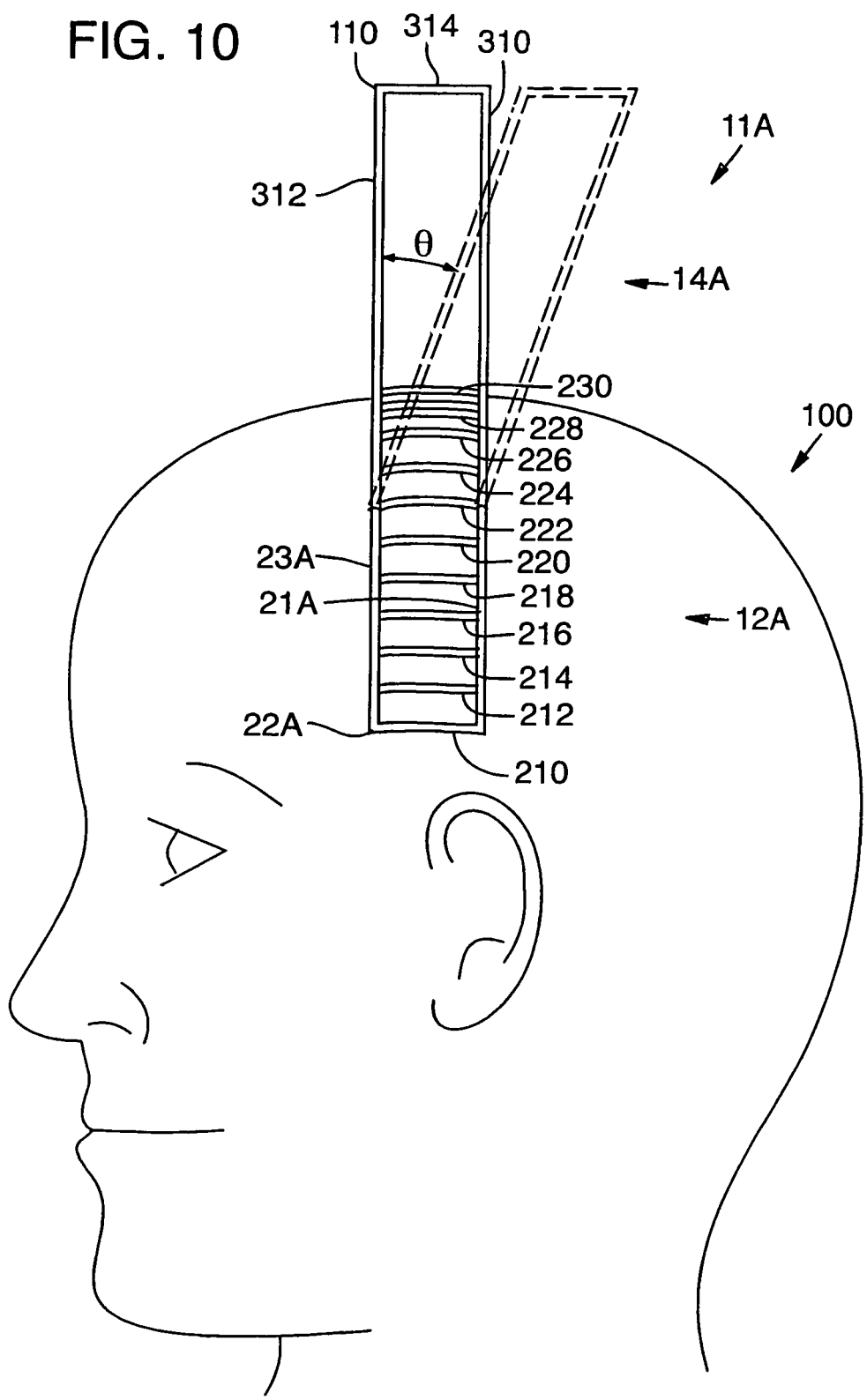
FIG. 10 is a side view of the device of FIG. 8.

An alternative embodiment of the device is illustrated at 11A in FIGS. 8-10 placed on a human head 100. Similar to the first embodiment (FIGS. 1-4) in many ways this alternative embodiment has a base 12A and extension portion 14A, where base 12A has a first end 22A and second end 24A, and a substantially arcuate, semicircular or semi-ovate shape along its length and width axes. However, in this embodiment, extension 14A includes a plurality of radially elongated extension elements 110, 112, 114, . . . 158, 160, rather than a minimal number of radially extending elongated elements 26, 28 (see FIGS. 1, 3 and 4). This embodiment includes twenty-six radially extending elongated extension elements 110, 112, 114, . . . 158, 160, although alternative embodiments may employ a different number of such elongated extension elements. As illustrated, the radially extending elongated elements 110, 112, 114, . . . 158, 160 are collected into four fan-like groupings 170, 172, 174, 176, and elongated elements 134 and 136 are connected by lateral elements 180 and 182.

As illustrated in FIG. 9 elongated elements 110, 112, 114, . . . 158, 160 may extend substantially orthogonally from base 12A or, as illustrated by the dotted lines, may be offset from this orthogonal orientation at an angle, θ. The degree of offset (θ) may be up to 60 degrees to either side of the base, such as less than about 45 degrees, or less than about 30 degrees. In particular embodiments, the degree of offset is about 20 degrees. Either all, some, or none of the elongated elements may be offset. In some embodiments, alternate elongated elements are offset. For example, elongated elements 112, 116, 120 . . . 156, 160 may be offset 20 degrees, while elongated elements 110, 114, 118, . . . 154, 158 may be oriented substantially orthogonally to base 12A.

Figure 4:
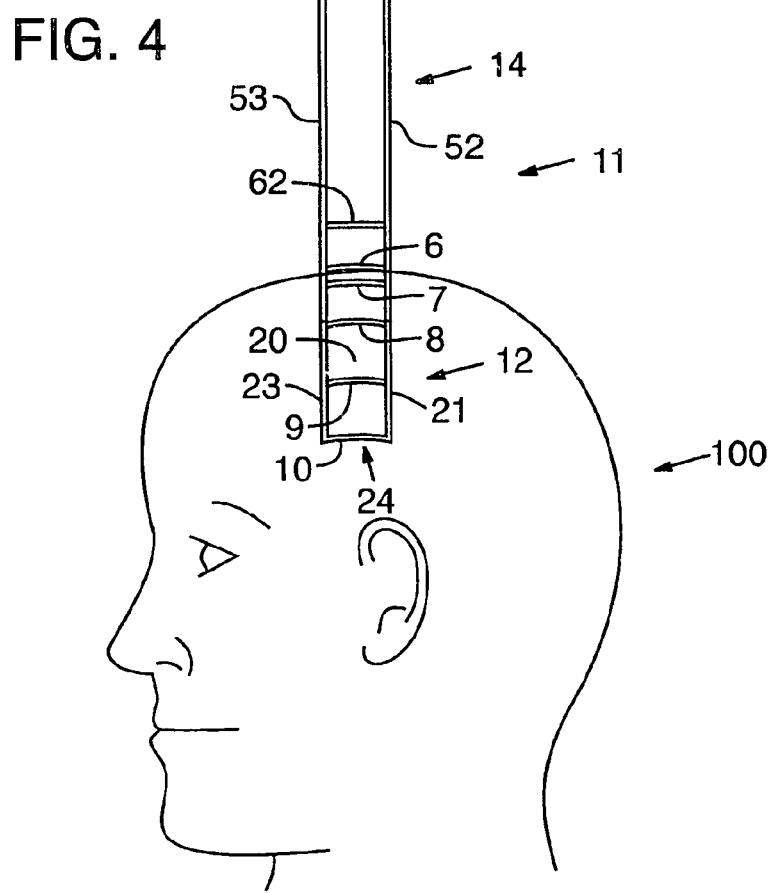
FIG. 4 illustrates a side view of the device of FIG. 1.

Similar to the extension portion illustrated in FIGS. 1, 3 and 4, the extension illustrated in FIGS. 8-9 may be a unibody element or a construction of plural components.

Similar to base 12 illustrated in FIGS. 1, 3 and 4, base 12A illustrated in FIGS. 8-9 includes a pair of substantially parallel, arcuate, elongate, longitudinally-extending, laterally spaced frame members 21A and 23A. Extending between and interconnecting longitudinal frame members 21A and 23A are twenty-six elongate, arcuate transverse frame members 210, 212, 214, . . . 258, 260.

The amount of surface charge, and the influence of that surface charge on the deeper tissues of the subject's body that are stimulated, depends on the overall lengths and locations of the electrical components which contain radial components. In this embodiment, the overall length of such radial elements is reduced and their distances from the subject's body are increased, relative to the embodiment shown in FIGS. 1-4. In other words, the ratio of the total length of the coil extending radially from the base to the total length of the coil associated with the base is less than the corresponding ratio in other embodiments, such as the embodiment illustrated in FIGS. 1-4.

Referring to the extension element shown in FIG. 9, which is exemplary of the other extension elements, it includes a pair of elongate, substantially parallel spaced elongate extension frame members 310 and 312, with each frame member connected to one of laterally spaced frame members 21A and 23A. The first ends of the extension frame members, such as 310, are connected to spaced apart locations on frame member 21A, while the first ends of extension frame members, such as 312, are connected to spaced apart locations on frame member 23A. The second, or outer, ends of the extension frame members, such as 310 and 312, are interconnected by transverse spacer frame members, such as 314.

In this second embodiment, base 12A includes twenty-six transverse elements 210, 212, 214, . . . 258, 260 (which may be referred to as "strips"), compared to the ten transverse elements 1-10 of the first embodiment (see FIG. 1). Extension 14A of this second embodiment includes twenty-six elongated elements 110, 112, 114, . . . 158, 160 grouped into four fan-like collections 170, 172, 174, 176. These elongated elements 110, 112, 114, . . . 158, 160 are coupled to base 12 at locations adjacent certain transverse elements 210, 212, 214, . . . 258, 260. For example, as illustrated in FIG. 8, elongated elements 110, 112, 114, 116, 118, and 120 are coupled to base 12A adjacent transverse element 222; elongated elements 122, 124, 126, 128, 130, 132 and 134 are coupled to base 12A adjacent transverse element 226; elongated elements 136, 138, 140, 142, 144, 146, and 148 are coupled to base 12A adjacent transverse element 244; and elongated elements 150, 152, 154, 156, 158, 160 are coupled to base 12A adjacent transverse element 248. In alternative embodiments, however, each elongated element may be coupled to the base in a different arrangement. Each elongated element may be separately coupled to the base adjacent a single transverse element, or different numbers of elongated elements may be grouped together and coupled to the base adjacent certain transverse elements. For example (and without limitation), pairs of elongated elements may be coupled to the base adjacent every other transverse element, or groups of multiple elongated elements may be coupled to the base adjacent six individual transverse elements.

The elongated elements 110, 112, 114, . . . 158, 160 within an individual fan 170, 172, 174, and 176 may be regularly spaced apart from, or angularly disposed relative to, each other. For example (and without limitation), as shown in FIG. 8, the elongated elements of fans 170 and 176 are spaced apart, or angled, from each other by about 8 degrees, while the elongated elements of fans 172 and 174 are spaced apart from each other by about 6 degrees.

As in the first embodiment, the longitudinally-extending laterally spaced frame members, 21A and 23A, may be oriented substantially parallel to each other, or may be placed in a non-parallel orientation.

Figure 11:
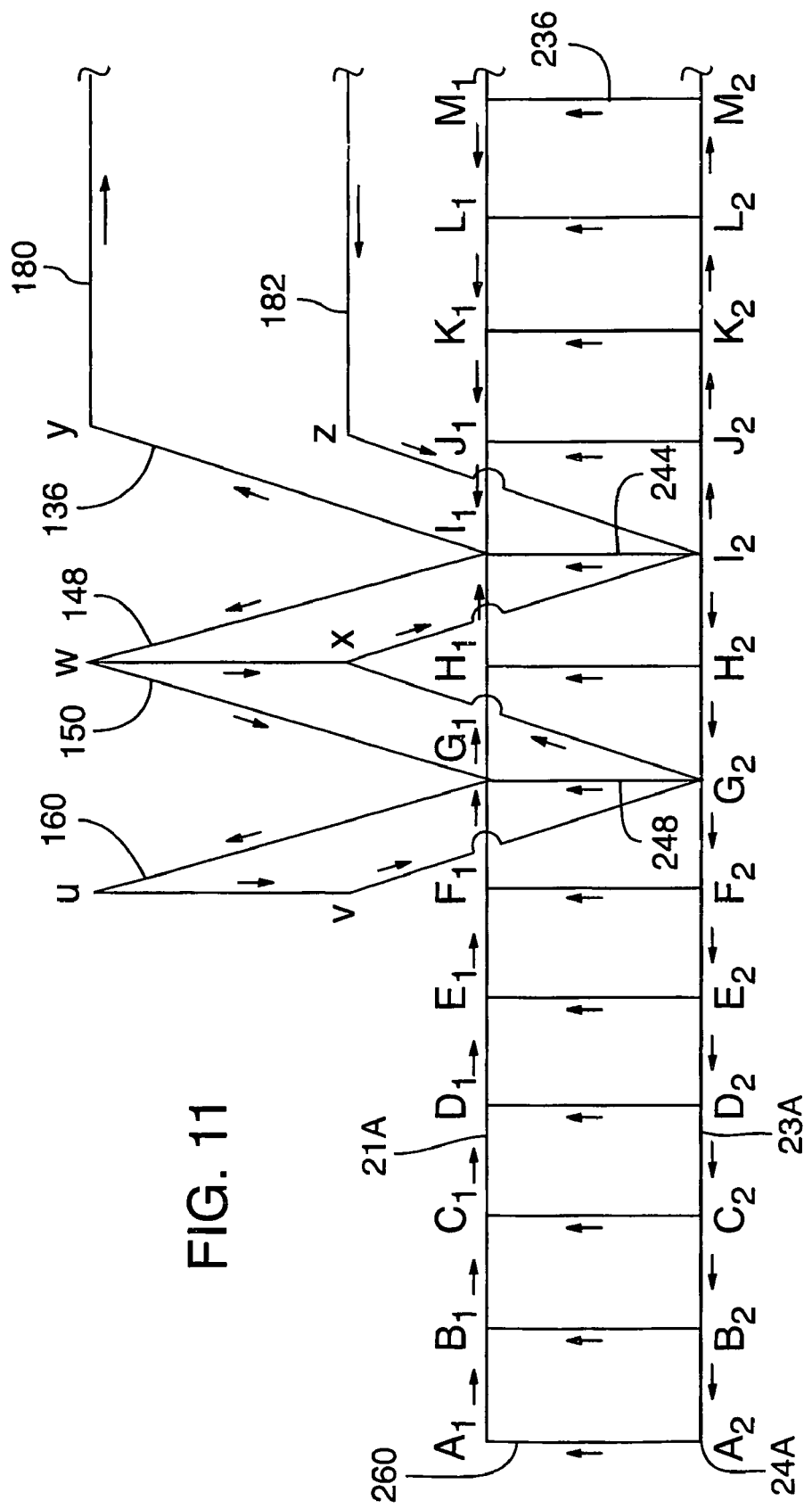
FIG. 11 is a partial schematic of the flow of electricity through the windings of the device illustrated in FIGS. 8-9. This schematic is not an electrical circuit diagram. For clarity, only a few of the radially extending elements are shown.

FIG. 11 is a schematic illustration of current flow through the windings of the embodiment illustrated in FIG. 8, with reference numerals correlating these windings to certain structures illustrated in FIGS. 8-10. FIG. 11 is not a circuit diagram in the true sense-this illustration simply shows how a coil for the device may be made from individual windings of the coil, with each individual winding comprising a circuit. For the sake of clarity, only part of the entire device is shown. Additionally, FIG. 11 illustrates only one exemplary, non-limiting pattern of current flow. Other embodiments may exhibit a different pattern of current flow due to a different placement of windings, and in particular embodiments, the windings are connected in series and current passing through the strips of the base (i.e., flowing through the windings associated with the transverse elements of the base between the lateral frame members) flows in the same direction.

As illustrated in FIG. 11, the direction of electrical current flow is the same in all of the twenty-six strips of the base 12A (illustrated in FIGS. 8-10); flowing in a direction from the lateral frame member 23A to lateral frame member 21A. Generally, current to this portion of the coil arrives at Z, travels down to $I_2$, and flows through strips $J_2$-$J_1$, $K_2$-$K_1$, $L_2$-$L_1$, and $M_2$-$M_1$. Each strip ($A_2$-$A_1$, $B_2$-$B_1$, ... $M_2$-$M_1$) has a return path through an elongated element 110, 112, 114, ... 158, 160 of one of the fan-like groupings 170, 172, 174, 176. For example, the return path for strip $J_2$-$J_1$ may be elongated element 140 (not shown in FIG. 11). The current flow to $I_2$ then flows through strip $H_2$-$H_1$ and to $I_1$. From here, the current flows up the extension to W. then to X (the line W-X representing the junction of two elongated elements, 148 and 150), then to $G_2$, then through strips $F_2$-$F_1$, $E_2$-$E_1$, $D_2$-$D_1$, $C_2$-$C_1$, $B_2$-$B_1$, $A_2$-$A_1$, and returns to $G_2$. Each of strips $F_2$-$F_1$, $E_2$-$E_1$, $D_2$-$D_1$, $C_2$-$C_1$, $B_2$-$B_1$, $A_2$-$A_1$, has a return path through an elongated element of fan-like collection 176 composed of elongated elements 150-160. For example, the return path for strip $F_2$-$F_1$, is shown by the $G_1$-U-V-$G_2$ path corresponding to elongated element 260 in FIGS. 8-9. Other strips (e.g., E2-E1, D2-D1, C2-C1) have return paths through other elongated elements (not shown in FIG. 11) anchored at the G2-G1 strip (i.e., elongated elements that are part of fan-like collection 176, shown in FIGS. 8-9). After flowing through the strips and return paths, the current flows to $G_1$, then to W (through another winding, against the illustrated arrow), on to X, back to $I_2$, then $I_1$, and returns to the other end of the device (not shown) via Y.

The return path of current flow is in the opposite direction of the strips, although these return paths of the coil associated with base 12A (i.e., along transverse elements 210, 212, 214, ... 258, 260) are physically spaced apart from base 12A by associating the return paths with transverse spacer frame members, such as 314 in FIG. 9, of extension 14A. The physical distance between the strips and return paths may be any suitable distance, such as about 1 cm, 5 cm, 10 cm, or more. In certain embodiments, the return paths are separated from the strips by a distance of at least about 5 cm; for example, as illustrated in FIG. 9, the physical distance between the portion of the coil in base 12A at transverse element 210 and the return path of the coil along transverse spacer frame member 314 is at least about 5 cm.

Similar to the first embodiment illustrated in FIGS. 1-4, this second embodiment may include a frame made of flexible or malleable material, for example, to conform base 12A to the shape of a subject's skull, and may include a cushion placed adjacent to the underside of base 12A for providing an additional measure of comfort for a subject. Additionally, the device may contain a shield or screen that inhibits or blocks the magnetic fields of extension 14A.

Thus, as in the embodiment illustrated in FIGS. 14 and 8-10, the components of base 12A and extension 14A may form an electrical coil, either by using frame elements that are electrical transducers or associating a transducer (such as a wire) with the frame (e.g., as illustrated in FIG. 5 and discussed above). The extension portion 14A provides a return path for the electricity flowing through the base 12A. As in the first embodiment (FIGS. 1-4), extension portion 14A of this second embodiment places electrical currents flowing through the return paths away from the subject, to reduce their electrical effect on the body tissues of the subject. In embodiments where the coil comprises one or more windings of electrically conductive material (e.g., metal bands or wires), the wire and frame elements may demonstrate the configuration illustrated in FIG. 5.

The device described above can be used in a variety of ways and on any part of a subject's body. Any conductive tissue, including (but not limited to) nervous tissue and muscle tissue, may be stimulated by the device. The device creates a time-varying magnetic field capable of penetrating the body of a subject that, in turn, can induce an electric field within a conductive tissue of the body. These induced electric fields may stimulate such conductive tissues. For example, the device is capable of depolarizing a neuron within the body of the subject, including neuron comprising the central nervous system, such as those found in the brain.

The device may be used on any appropriate subject. For example, the device may be used on humans for treating or studying certain physiological conditions, such as neurophysiological or cardiovascular conditions, or for studying the physiology of the body. The device also may be used in similar ways on other types of animals, including mammals, such as canines, felines, rodents, or primates.

Since magnetic stimulation can alter blood flow, the device may be used for studying or treating cardiovascular conditions in various tissues of a subject's body. For example, the device illustrated in FIG. 1 may be used in TMS applications to monitor or regulate blood flow through the brain of a subject, such as a subject at risk for suffering a stroke. Additionally, the device may be used to monitor or to regulate blood flow during reperfusion following a cardiovascular event, such as stroke or other blockage of a blood vessel. The device may be used for studying treating cardiovascular conditions associated with parts, tissues, or organs of the body other than the brain, such as the heart, lungs, kidneys, liver, and spinal cord.

This device may be used to study or treat a neurophysiological condition associated with the deep regions of the brain. A "neurophysiological condition" may be a pathological neurophysiological condition or a neurophysiological disorder, such as (but not limited to): clinical depression, non-clinical depression, dysthemia, bipolar disorder, drug addiction, substance abuse, anxiety disorder, obsessive compulsive disorder, or Parkinson's disease. The device also is useful for treating addiction, such as drug addiction, or other substance abuse, such as alcoholism.

The deep region of the brain includes the nucleus accumbens, and may include other structures such as the ventral tegmentum; the amigdala; and the medial prefrontal and cingulate cortexes. The prefrontal and cingulate cortexes are connected to the nucleus accumbens by dense neuronal fibers, and these fibers are known to play an important neurophysiological role in substance abuse and drug addiction. Therefore, stimulating these dense neuronal fibers is one way to use the device to treat such neurophysiological conditions.

The focus of magnetic field generated by the device coil may be altered by changing the base. For example, as the width of the base is narrowed, the magnetic field will narrow, thus stimulating a narrower area of tissue. Additionally, narrowing the width of the base will decrease the depth of the field produced by the coil. Therefore a sufficiently focused coil can stimulate selected regions of the body. For example, the coil embodied in FIGS. 1-5, and placed accordingly, is capable of stimulating the deep regions of the brain and the coronal section underneath the base, but would not stimulate the frontal or occipital lobes of the brain. However, if the coil was placed at a different portion of a subject's skull (e.g., at the base of the skull, wrapping behind the subject's head) then a different part of the brain might be stimulated (e.g., the occipital lobe).

One embodiment for using the device comprises identifying a subject suffering, or at risk of suffering, a neurophysiological condition; providing an electrically conductive coil as described above (i.e., having a partially toroidal or ovate base with a concave first side to be directed toward a body part of the subject); placing the coil external to the subject's skull; electrically connecting a power supply to the coil; and activating the coil to stimulate the deep region of the subject's brain.

The device also may be used for treating a neurophysiological condition by identifying a subject suffering a neurophysiological condition and providing an electrically conductive coil (as described above). The coil is placed external to the subject's skull and activated to stimulate the deep region of the subject's brain. In particular embodiments, the coil has a partially toroidal or ovate base portion with a concave first side to be directed toward a body part of a subject and has an extension portion projecting outwardly from a second side opposite the first side. In alternative embodiments, the coil has a base portion and an extension portion, the extension portion comprising a radially elongated extension element;

Another embodiment comprises identifying a subject; providing an electrically conductive coil as described above; placing the coil external to the subject's skull; electrically connecting a power supply to the coil; activating the coil to stimulate the deep region of the subject's brain; and localizing and characterizing brain function. For example, the coil could be used in combination with brain imaging, such as magnetic resonance imaging (MRI) or positron emission tomography (PET), to study the effect of deep brain stimulation on other regions of the brain. Additionally, the subject may be directed to carry out some task, including (but not limited to) speaking, reading, writing, or sleeping. For example, the subject can be directed to move a specific body part, such as an arm or leg, in order to study the relevant neuronal circuits in the brain. As another example, the subject can be directed to look at different intensities of light, or different shapes, in order to study the neuronal circuits of the brain associated with vision. Additionally, the subject can be instructed to perform some mathematical task to study higher brain functions. As another example, the coil may be used in conjunction with brain imaging to study the effects of personal spiritual practices, such as yoga, meditation, or prayer.

Yet another embodiment comprises non-invasively stimulating a subject's brain. "Non-invasively" means the subject's brain, including the deep regions of the brain, can be stimulated with the device coil placed externally of the subject's skull. In other words, the subject's brain, including the deep regions of the brain, can be stimulated without placing the coil in an orifice of the subject's head, such as the mouth, or introducing the coil into the subject's skull via a surgical procedure.

In some embodiments, a train of electromagnetic pulses is administered to the subject. Individual pulses measuring from about 50 to about 2000 microseconds in duration are produced by the coil, and the pulse length may be altered according to various factors including (but not limited to) the tissue stimulated, the particular coil construction or shape, or the physiological condition of the subject. A duration of about 1000 microseconds is capable of stimulating nervous tissue.

The train may comprise an appropriate number of individual pulses administered over a certain period of time. In some embodiments, a train of about 1 to about 100 pulses is administered. Specific embodiments employ a number of pulses within a specific range, such as less than 100, less than 75, less than 25, or 25 to 50, 10 to 75, 5 to 100, 5 to 25, 25 to 75, or 75 to 100. Alternative embodiments employ a specific number of pulses, such as 75, 60, 50, 40, 25, 10, 5, 1, or any of 1 to 100.

The pulses may vary in frequency as well as number. Certain embodiments use a frequency range of from about 1 to about 100 Hz, while other embodiments employ pulses of from about 5 to about 60 Hz, or more particularly, from about 20 to about 30 Hz. Additionally, pulses within a train of pulses may be administered at different frequencies.

In some embodiments, two or more stimulator channels may be connected to the coil, which can create close interval pulses. In such embodiments, the interpulse interval may be one millisecond or longer in duraction. The use of multiple stimulator channels may allow differential stimulation of the brain by using different intensities or frequencies for stimulating different regions of the brain.

The train of pulses may be administered during a certain period of time, such as from about 1 to about 120 seconds. Particular embodiments involve administering the train of electromagnetic pulses during a period of time of from about 2 to about 60 seconds, or more particularly, a period of time of from about 20 to about 30 seconds. The delay between pulses may vary, but certain embodiments use delays of similar duration.

Embodiments of this method of treating or studying a particular condition of a subject also may involve administering a train (or plural trains) of electromagnetic pulses during a session. The entire treatment or study regimen may be conducted over an indefinite period of time, or may involve a certain number of sessions, such as from about 1 to about 30 sessions, over a certain period of time, such as 1 to 8 weeks, 2 to 7 weeks, 3 to 6 weeks, 4 to 5 weeks, less than one week, or longer than 8 weeks. Alternative embodiments employ a single session.

A plurality of trains may have an intertrain interval of time. Particular embodiments have an intertrain interval measuring from about 5 to about 240 seconds, from about 20 to about 180 seconds, or from about 60 to about 120 seconds. As just one non-limiting example, a plurality of electromagnetic pulse trains may be administered in the following manner: a train of 50 pulses over 60 seconds; an intertrain interval of 40 seconds; a train of 20 pulses over 120 seconds; an intertrain interval of 30 seconds; a train of 30 pulses over 60 seconds; an intertrain interval of 10 seconds; a train of 30 pulses over 90 seconds.

If the subject is suffering a specific condition, such as a neurophysiological condition, then the sessions may last until clinical improvement occurs. For example, the subject might be a human suffering clinical depression and the treatment may last until the subject no longer tests for clinical depression. As another example, the subject might be a human suffering drug addiction, and the treatment might last for a certain number of sessions until the person can manage his or her cravings for the drug.

The number of pulses, train length, and intertrain interval may be varied according to various factors including (but not limited to): the physiological condition of the subject; the characteristics of the subject; the condition being treated or studied; the construction of the coil; the type of generator or power supply used to generate the electromagnetic pulses; or the number of generators or power supplies used.

EXAMPLES

The following examples are provided to illustrate particular features of the present invention. The scope of the present invention should not be limited to the features illustrated by these examples.

Example 1

Considerations for a Transcranial Magnetic Stimulator Coil

A coil was designed for deep brain stimulation in accordance with the present invention.

In order to develop a TMS coil for stimulation of deep brain regions, several factors were considered. For TMS stimulation, a brief, but strong current should be passed through a coil of wire, generating a time-varying magnetic field (B). An electric field (E) is generated at every point within the magnetic field (B), having a direction perpendicular to the magnetic field (B) and proportional to the time-rate of change of the vector potential (A(r)). The electric field (E) induced by the magnetic field (B) induces action potential in excitable neuronal cells, which in turn results in activation of neuronal circuits if an electric field (E) above certain threshold is created. The resulting induced electric currents are proportional to the electric field (E) amplitude.

The vector potential A(r) in position r is related to the current I in a wire (I) by the expression:

$$A(r) = \frac{\mu_0 I}{4\pi} \int \frac{dl'}{|r-r'|} \quad (1)$$

Where $\mu_0 = 4\pi * 10^{-7}$ Tm/A is the permeability of free space, T is tesla, m is meters, and A is ampere. The integral of dl' is over the wire path, where dl' is an element of wire, and r' is a vector indicating the position of the wire element.

The magnetic and electric fields resulting from the current in the wire ($B_A$ and $E_A$ respectively) are related to the vector potenti $$B_A = \nabla \times A(r) \quad (2)$$

where $\nabla \times$ is curl, and:

$$E_A = -\frac{\partial A(r)}{\partial t} \quad (3)$$

where t is time.

Under these equations, the current (I) is the only variable changing over time. Hence, the electric field $E_A$ can be described as:

$$E_A = \frac{\mu_0}{4\pi} \frac{\partial I}{\partial t} \int \frac{dl'}{|r-r'|} = C \int \frac{dl'}{|r-r'|} \quad (4)$$

with $C = \frac{\mu_0 \partial I}{4\pi \partial t}$

Since brain tissue has conducting properties, while the air and skull are almost complete insulators, the vector potential will induce accumulation of electric charge at the brain surface. This surface charge ($E_\Phi$) is another source for the electric field (E) and can be expressed as:

$$E_\Phi = -\nabla \Phi$$

where $\nabla$ is divergence and $\Phi$ is the scalar potential produced by the surface electrostatic charge.

The total electric field in the brain tissue (E) is the vectorial sum of these two fields:

$$E = E_A + E_\Phi \quad (6)$$

The surface electrostatic field ($E_\Phi$) generally opposes the induced field ($E_A$). Consequently, as the strength of the electrostatic field ($E_\Phi$) increases, the strength of the total field (E) decreases. However, the amount of surface charge produced (and, hence, the magnitude of $E_\Phi$) correlates to coil orientation.

If an electric field (E) is generated by a coil placed external to the skull, certain parts of that field will lie parallel or tangential to the skull of the subject, while other parts of the electric field (E) will lie perpendicular to the skull of the subject. The perpendicular components will induce a surface charge ($E_\Phi$) at the surface of the brain. As the magnitude of surface charge ($E_\Phi$) increases, the magnitudes of the perpendicular parts of the electric field (E) decrease. A sufficiently large surface charge ($E_\Phi$) would completely cancel out the perpendicular parts of the field, so only the parallel parts of the total field (E) would remain. See, Tofts, P. S., *Phys. Med. Biol.*, 35:1119-28 (1990); Tofts, P. S. and Branston, N. M., *Electroencephal. Clin. Neurophysiol.*, 81:238-9 (1991). This cancellation of the perpendicular parts of the field is a direct consequence of Maxwell equations with the appropriate boundary conditions.

If a surface charge ($E_\Phi$) does exist, the parallel components of the total electric field (E) generated by a coil placed external to the skull diminish in strength within the tissue. For example, it has been reported that, for a simple model of the brain as a flat homogeneous volume conductor, the surface field can reduce the strength of the total field resulting from a circular coil placed perpendicular to the tissue (i.e., the coil is placed on its edge against the tissue) by 42% along a line perpendicular to the surface and passing through the center of the coil. See, Roth, B. J., et al., *Muscle Nerve*, 13:734-41 (1990); Tofis, P. S. and Branston, N. M., *Electroencephal. Clin. Neurophysiol.*, 81:238-9 (1991).

Thus, as the perpendicular field produced by any coil increases, more surface charge is induced, thus diminishing the total electric field in the tissue. Therefore, coils capable of stimulating deep brain regions produce significant field strength in directions parallel to the surface with reduced perpendicular components of the induced field. The embodiment illustrated in FIGS. 1-5 accomplishes these objectives by employing a substantially toroidal or ovate shaped base where the coil portions along the length and width axes of the base lie parallel to the skull of the human subject.

Example 2

Comparison with Known Coil Designs

A coil produced according to the present invention and under the considerations of Example #1 is compared to available known coils with respect to their suitability for activating deep brain regions.

Known coils can stimulate cortical or peripheral nerves, but the electric fields induced by such known coils decrease rapidly as distance from the coil increases. For example, the electric field induced by a 9.2 cm diameter circular known coil was measured using a volume conductor filled with saline. The coil was placed parallel to the surface of the volume (i.e., the coil was placed as flat as possible against the volume, rather than placing it edge-on against the volume). See, Maccabee, P. J., et al., *Electroencephal. Clin. Neurophysiol.*, 76:131-41 (1990). The field induced at a distance of 2.5 cm from the coil was less than 60% of the field induced at a distance of 0.5 cm from the coil. Moreover, the field induced at a distance of 4.0 cm from the coil was less than 40% of the field at induced at a distance of 0.5 cm from the coil. Id.

For a FIG. 8 coil, the field strength decreases more rapidly. For example, a FIG. 8 coil having two rings, each 4.8 cm in diameter, oriented parallel to (i.e., placed flat against) the conductor surface, induced a field at 2.5 cm from the coil center that was about 30% of the field at 0.5 cm from coil center. Id. Similar results were obtained in mathematical calculations of the induced electric field. See Cohen, L. G., et al., *Electroencephal. Clin. Neurophysiol.*, 75:350-7 (1990). While the use of an array of circular or FIG. 8 coils placed parallel to the skull can, in some cases, improve the focality of the field at the cortex, multiple coils will not counteract this rate of decrease in field strength with increasing distance from the coil. See Ruhonen, J., and Ilmoniemi, R. J., *Med. Biol. Eng. Comput.*, 38:297-301 (1998).

Placing a circular coil perpendicular to a skull surface (i.e., standing the coil on edge against the skull) may allow increased percentage strength of the field at a depth, relative to the field strength at the surface, compared to placing the coil parallel to (i.e., flat against) the skull surface. Tofts, P. S., *Phys. Med. Biol.*, 35:1119-28 (1990); Tofts, P. S. and Branston, N. M., *Electroencephal. Clin. Neurophysiol.*, 81:238-9 (1991). However, the absolute magnitude of the field, both at the surface and in deep regions of the brain, is reduced due to accumulation of charge at the surface (as described in Example 1), since a coil placed perpendicular to the skull surface will generate a field largely perpendicular to the skull surface, thus generating a greater surface charge ($E_\Phi$).

Another coil, termed a "slinky coil" is composed of several windings in intermediate orientation between FIG. 8 coil and a circular coil. See, Ren, C., et al., *IEEE Trans. Biomed. Engineering*, 42:918-25 (1995); Zimmermann, K. P., and Simpson, R. K. *Electroencephal. Clin. Neurophysiol.*, 101: 145-52 (1996). If placed on the surface of a subject's skull, a slinky coil may achieve a greater field magnitude and better focality at the brain surface near the coil center, but—like the circular and FIG. 8 coils—a slinky coil generally does not induce an electric field at a distance sufficient to stimulate the deep regions of the brain.

The coil of the present invention was compared to other coils using computer simulations of electric field distribution in a spherical conductor. The computer simulations were conducted using the Mathematica program (Wolfram, 1999). In these simulations, a subject's skull was modeled as a spherical homogeneous volume conductor with radius of 7 cm. The induced electrical field ($E_A$) and electrostatic surface field ($E_\Phi$), at specific points inside the spherical volume, were computed for several coil configurations using the method presented by Eaton. Eaton, H., *Med. Biol. Engineering and Computing*, 30:433-40 (1992).

The simulations revealed that, in coil configurations having perpendicular current components, accumulating surface charge diminishes total field strength. The presence of a surface electrostatic field not only reduces the total field strength at any point, but also leads to significant reduction in the relative strength of the total field (relative to total field strength at the surface) with increasing distance.

Figure 6:
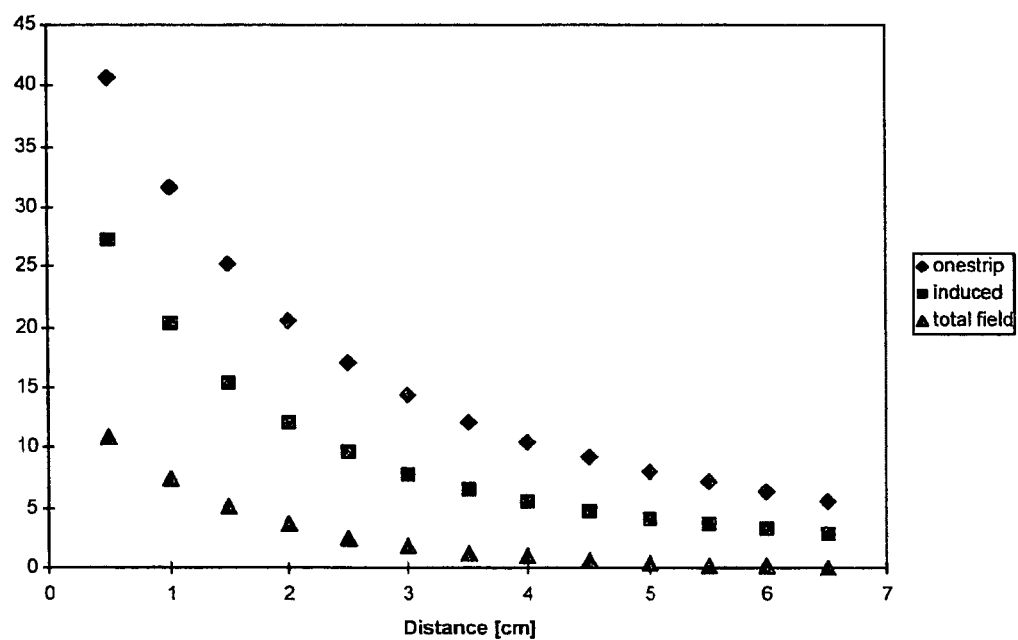
FIG. 6. is a graph comparing field strengths of a known coil with a single winding of the coil in the embodiment illustrated in FIGS. 1 and 2.

FIG. 6 is a plot of field strengths E (measured in V/m) for the z-components of the induced electric field (rectangles) and total electric field (triangles) of a one turn circular coil with diameter of D=5.5 cm placed perpendicular to the head. The z-components of the induced and total electric fields are the components lying in a direction tangential to the coil at its center. The electric field was measured in Volt/meter, and the rate of current change in all the calculations was taken as $\partial I/\partial t = 1000$ Amper/100 microseconds. These components are plotted as a function of distance from the coil along a central line perpendicular to the surface that passes through coil center.

For comparison purposes, the FIG. 6 graph also depicts the z-component of the total field strength generated by a single winding (e.g., winding number 5) of the coil illustrated in FIGS. 1 and 2, termed a "onestrip" coil. As above, the z-component refers to the electric field components lying in a direction tangential to the strip at its center. The portions of the onestrip coil near the surface of the skull lie substantially parallel to the surface of the skull and, thus, little or no surface charge is induced. Thus, the total field strength largely represents the strength of the induced field.

Figure 7:
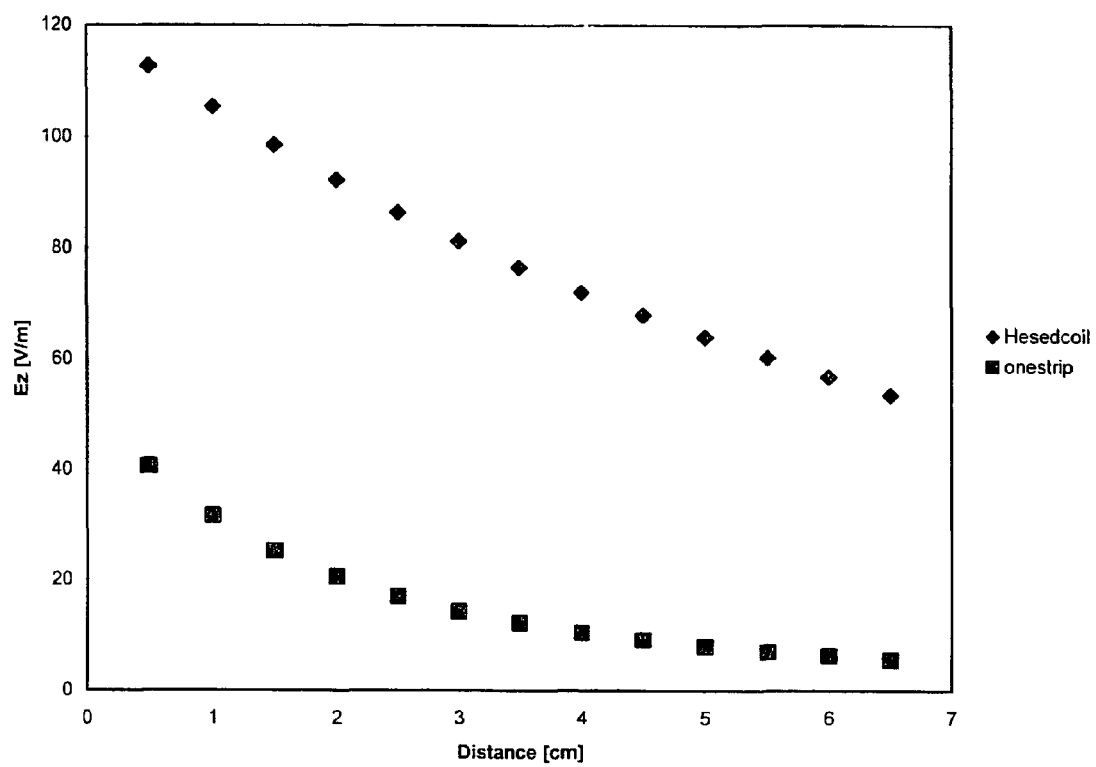
FIG. 7 is a graph comparing the field strengths of a single winding and the entire set of windings of the coil in the embodiment illustrated in FIGS. 1 and 2.

FIG. 7 is a graph comparing the field strength of the onestrip coil with the entire coil illustrated by FIGS. 1 and 2 (i.e., all ten windings), termed the "Hesedcoil," where each winding has one wire. As shown by this graph, this version of the Hesedcoil can produce an induced electric field of approximately 60 V/m at a distance of 6 cm from the coil, thus surpassing the threshold activation potential for neurons at these depths in the brain. Embodiments of the Hesedcoil having more wires, in several or all of the windings, may produce stronger electric fields at such distances.

Example 3

Analysis of a Second Embodiment

Similar to Examples 1 and 2, a second embodiment of the coil, illustrated in FIGS. 8-10, was analyzed for its ability to stimulate deep regions of the brain.

Theoretical computerized calculations were preformed using the Mathematica program as described above, assuming a conductive sphere with a radius of 7 cm. Additionally, measurements of a model of the human skull (average diameters: 15 cm×18 cm×23 cm), constructed from glass and filled with a saline solution, were preformed using a pickup probe for measuring the electric field in the Z direction in different spots within the model skull. For all measurements and calculations, the rate of current change was taken as 10000 Amper/100 microsec (which is approximately the maximal power output of standard, commercially available electrical stimulators). The field is described in Volt/meter.

According to the theoretical calculations, the maximal electric field within the brain was found to be adjacent to the middle of transverse element 260, as shown in FIG. 8. This theoretical calculation was confirmed by measurements of the model brain. Since this area represents the maximal electric field, the percentage of field strength at certain depths within the brain was measured relative to this location. Using the model brain, a pickup probe was moved along a line between the centers of transverse elements 260 and 210, and similar measurements were taken using the theoretical model.

As shown in FIGS. 11 and 12, the actual electric field induced in the model brain (designated as the "phantom brain" in FIGS. 11 and 12 and represented by open circle notations on the charts) was slightly lower compared to the theoretical calculations (represented by filled circle notations on the charts). FIG. 11 is a graph showing actual field strength, while FIG. 12 shows field strength expressed as a percentage of the maximal field in the brain cortex. The maximal field in the brain cortex was measured at 1 cm from transverse element 260, which is identified as "strip 26" in FIG. 12.

The very slight discrepencies between the theoretically expected field strengths at certain distances from the coil and the actual measured field strengths may have resulted from the fact that the actual coil used did not have a completely flexible frame and, therefore, not all of transverse elements 210, 212, 214, . . . 258, 260 would have been positioned strictly parallel to the model skull surface. Additionally, the extension portion of the device used differed from the embodiment illustrated in FIGS. 8-10 by having narrower separations between adjacent elongated elements 110, 112, 114, . . . 158, 160.

Theoretical calculations of the effect of screening the return paths of the extension portion with pieces of metal were also performed (though these measurements were not made with the existing model). As shown in FIGS. 11-12, placing a metal screen around the return paths (i.e., around some or all of the frame elements making up the extension portion) can contain the magnetic fields induced by these portions of the coil and, therefore, reduce interference with the electric field induced by the base portion of the coil. Furthermore, these calculations show that such screening would not only increase the total field induced anywhere in the brain, but also increase the strength of the field at certain depths relative to the surface field strength in the cortex of the brain.

While the present invention is described in connection with at least two embodiments, the scope of the present invention is not intended to be limited to any particular embodiment. Instead, the descriptions and examples disclosed are intended to cover all alternatives, modifications, and equivalents that may be included within the spirit and scope of the invention as defined by the claims.

We claim:

1. A magnetic stimulator for placing externally of a body part of a subject and operable to induce currents within the body, comprising:
    an electrically conductive coil, where the coil comprises a base portion and an extension portion, the extension portion comprising plural extension elements projecting outwardly from the base portion,
    wherein the base portion comprises multiple stimulating elements and wherein the extension portion comprises multiple return elements for return paths for current in the stimulating elements, the return elements being spaced from the stimulating elements so that the electrical effect of the return path current on the body part is reduced.

2. The magnetic stimulator according to claim 1, further comprising a frame.

3. The magnetic stimulator according to claim 2 where the coil comprises a winding associated with the frame.

4. The magnetic stimulator according to claim 1 where the base portion has a length axis and a width axis, the coil in the base portion comprising elements spaced apart and transverse to the length axis such that the flow current in these elements is in substantially the same direction.

5. The magnetic stimulator according to claim 4 where the base portion is a partially toroidal or ovate base.

6. The magnetic stimulator according to claim 4 where the base portion comprises plural laterally spaced frame members extending along the length axis.

7. The magnetic stimulator according to claim 6 where at least two of the laterally spaced frame members are in a substantially non-parallel orientation.

8. The magnetic stimulator according to claim 1 where at least two extension elements are coupled to the base portion adjacent each other.

9. The magnetic stimulator according to claim 8 where the extension elements are angularly disposed relative to each other.

10. The magnetic stimulator according to claim 1 where the plural extension elements comprise at least two groups of plural extension elements, where the extension elements of the same group are coupled to the base portion adjacent each other.

11. The magnetic stimulator according to claim 1 where an extension element comprises a pair of substantially parallel spaced elongate extension frame members, each extension frame member having an inner end and an outer end, the inner ends of the extension frame members coupled to the base portion, the outer ends of the extension frame members interconnected by a transverse spacer frame member.

12. The magnetic stimulator according to claim 1, further comprising a shield at least partially enclosing the extension portion.

13. The magnetic stimulator according to claim 1, further comprising a power supply electrically connected to the coil.

14. The magnetic stimulator according to claim 1 where the base has a concave first side configured to be complementary to the cranium of a subject.

15. The magnetic stimulator according to claim 1 where the coil comprises means for inducing an electric field within the deep region of the brain.

16. The magnetic stimulator of claim 1, wherein the body part is a skull.

17. The magnetic stimulator of claim 1, wherein the extension portion is configured to place electrical currents flowing through return paths away from the region of the body part having the induced currents.

18. The magnetic stimulator of claim 1, wherein the base portion comprises plural longitudinally-extending laterally spaced frame members.

19. The magnetic stimulator of claim 1, wherein a majority of the current flowing through the base portion is oriented substantially in a single direction.

20. A method of treating a neurophysiological condition, comprising:
    identifying a subject suffering a neurophysiological condition;
    placing a magnetic stimulator external to the subject's skull; and activating the coil to stimulate the deep region of the subject's brain,
    the magnetic stimulator comprising a base with a first side to be directed toward a body part of a subject, the base comprising multiple substantially parallel stimulating elements configured to conduct electrical current in substantially a single direction of current flow, thereby inducing electrical fields within the body part, and an extension portion projecting from a second side of the base and comprising multiple respective return elements for return paths for the current in the stimulating elements, the return elements being spaced from the stimulating elements so that the electrical effect of the return path current on the body part is reduced.

21. The method according to claim 20 where the neurophysiological condition is clinical depression, non-clinical depression, dysthymia, bipolar disorder, drug addiction, substance abuse, anxiety disorder, obsessive compulsive disorder, or Parkinson's disease.

22. A magnetic stimulator for placing externally of a body part of a subject and operable to induce currents within the body, comprising:
  a base with a first side to be directed toward a body part of a subject, the base comprising multiple substantially parallel stimulating elements configuTed to conduct electrical current in substantially a single direction of current flow, thereby inducing electrical fields within the body part; and
  an extension portion projecting from a second side of the base and comprising multiple respective return elements for return paths for the current in the stimulating elements, the return elements being spaced from the stimulating elements so that the electrical effect of the return path current on the body part is reduced.

23. The magnetic stimulator of claim 22, wherein the stimulating elements are complementary in shape and tangential to the surface of the body part when the magnetic stimulator is placed on the body part.

24. The magnetic stimulator of claim 22, wherein a majority of the current flowing through the base is oriented substantially in the single direction.

25. The magnetic stimulator of claim 22, wherein the respective return elements comprise current pathways configured to carry the current in a direction substantially opposite the current in the stimulating elements.

26. The magnetic stimulator of claim 22, wherein at least some of the respective return elements in the extension portion are spaced from their associated stimulating elements in the base by at least 5 cm.

27. The magnetic stimulator of claim 22, further comprising a shield placed around at least a portion of the extension portion, the shield being capable of inhibiting magnetic fields produced in the extension portion.

28. The magnetic stimulator of claim 22, where the base and the extension portion are part of one or more electrically conductive coils comprising one or more windings.

29. The magnetic stimulator of claim 22, where the extension portion is positioned off-center relative to the base.

30. The magnetic stimulator of claim 22, wherein the base is flexible or malleable.

31. The magnetic stimulator of claim 22, wherein the stimulating elements of the base are spaced apart from one another.

32. The magnetic stimulator of claim 22, wherein the base comprises substantially parallel, elongated frame members, and wherein the stimulating elements extend transversely between the frame members.

33. The magnetic stimulator of claim 22, wherein the extension portion is triangular and comprises at least two elongated extensions elements that extend away from the base and converge toward each other.

34. The magnetic stimulator of claim 22, wherein the extension portion comprises one or more extension elements projecting radially outwardly from the base.

35. The magnetic stimulator of claim 34, where an extension element comprises a pair of substantially parallel spaced elongate extension members, each extension member having an inner end and an outer end, the inner ends of the extension members coupled to the base, the outer ends of the extension members interconnected by a transverse member.

36. A method of treating or studying a cardiovascular condition, comprising:
  identifying a subject at risk of suffering a cardiovascular condition;
  placing the magnetic stimulator of claim 22 external to the subject's body; and
  activating the coil to stimulate the subject.

37. The method according to claim 36 where the cardiovascular condition comprises a cardiovascular event.

38. The method according to claim 37 where the cardiovascular event is a stroke.

39. A magnetic stimulator for placement externally of a body part of a subject and operable to induce currents within the body, the magnetic stimulator comprising:
  an arcuate base having an inner face and an outer face, wherein the base is shaped to conform to a body part on which it is to be externally placed,
  the base providing a plurality of stimulating current pathways for inducing the currents within the body, wherein the stimulating current pathways conduct current substantially in a single direction within the base to avoid return current pathways that flow in a direction opposite to the single direction and that would oppose or interfere with magnetic fields within the body produced by the stimulating current pathways; and
  an extension portion extending away from the base that provides the return current pathways,
  wherein the base comprises first and second spaced longitudinal sides and the stimulating current pathways extend transversely of the base between the first and second spaced longitudinal sides, and wherein current flows through the first and second longitudinal sides, the stimulating current pathways, and the extension portion.

40. A magnetic stimulator for placement externally of a body part of a subject and operable to induce currents within the body, the magnetic stimulator comprising:
  an arcuate base having an inner face and an outer face, wherein the base is shaped to conform to a body part on which it is to be externally placed,
  the base providing a plurality of stimulating current pathways for inducing the currents within the body, wherein the stimulating current pathways conduct current substantially in a single direction within the base to avoid return current pathways that flow in a direction opposite to the single direction and that would oppose or interfere with magnetic fields within the body produced by the stimulating current pathways; and
  an extension portion extending away from the base that provides the return current pathways,
  wherein the base comprises a pair of elongated members between which extend a plurality of the stimulating current pathways, and wherein the extension portion comprises one or more conductive elements that form a loop extending outwardly from the plane of the base.

41. A magnetic stimulator for placement externally of a body part of a subject and operable to induce currents within the body, the magnetic stimulator comprising:
  an arcuate base having an inner face and an outer face, wherein the base is shaped to conform to a body part on which it is to be externally placed,
  the base providing a plurality of stimulating current pathways for inducing the currents within the body, wherein the stimulating current pathways conduct current substantially in a single direction within the base to avoid return current pathways that flow in a direction opposite to the single direction and that would oppose or interfere with magnetic fields within the body produced by the stimulating current pathways; and an extension portion extending away from the base that provides the return current pathways, wherein the extension portion comprises a plurality of extension elements projecting outwardly from the base.

42. The magnetic stimulator of claim 41, wherein the stimulating current pathways are substantially parallel to one another and tangential to the external surface of the body part on which the magnetic stimulator is to be placed.

43. The magnetic stimulator of claim 41, wherein the stimulating current pathways are spaced apart from one another.

44. The magnetic stimulator of claim 41, wherein the base is flexible or malleable.

45. The magnetic stimulator of claim 41, wherein the extension portion is triangular and comprises at least two elongated extensions elements that extend away from the base and converge toward each other.

46. The magnetic stimulator of claim 41, wherein the extension elements project from the base.

47. The magnetic stimulator of claim 41, wherein the extension elements comprise pairs of substantially parallel spaced elongate members interconnected at their outward ends by transverse members.

48. A magnetic stimulator for placement externally of a body part of a subject and operable to induce currents within the body, the magnetic stimulator comprising:
   an arcuate base having an inner face and an outer face, wherein the base is shaped to conform to a body part on which it is to be externally placed,
   the base providing a plurality of stimulating current pathways for inducing the currents within the body, wherein the stimulating current pathways conduct current substantially in a single direction within the base to avoid return current pathways that flow in a direction opposite to the single direction and that would oppose or interfere with magnetic fields within the body produced by the stimulating current pathways;
   an extension portion extending away from the base that provides the return current pathways; and
   a shield positioned between the return pathways and the stimulating current pathways, the shield being configured to inhibit magnetic fields produced by the return pathways.

49. A method of studying or treating a neurophysiological condition, comprising:
   identifying a subject suffering a neurophysiological condition;
   placing a magnetic stimulator external to the subject's skull; and
   activating the magnetic stimulator to stimulate the deep region of the subject's brain, the magnetic stimulator comprising,
   an arcuate base having an inner face and an outer face, wherein the base is shaped to conform to a body part on which it is to be externally placed,
   the base providing a plurality of stimulating current pathways for inducing the currents within the body, wherein the stimulating current pathways conduct current substantially in a single direction within the base to avoid return current pathways that flow in a direction opposite to the single direction and that would oppose or interfere with magnetic fields within the body produced by the stimulating current pathways; and
   an extension portion extending away from the base that provides the return current pathways.

50. The method according to claim 49 where the neurophysiological condition is clinical depression, non-clinical depression, dysthymia, bipolar disorder, drug addiction, substance abuse, anxiety disorder, obsessive compulsive disorder, or Parkinson's disease.

51. A method of studying or treating a cardiovascular condition, comprising:
   identifying a subject at risk of suffering a cardiovascular condition;
   placing the magnetic stimulator of claim 41 external to the subject's body; and
   activating the coil to stimulate the subject.

52. The method according to claim 51 where the cardiovascular condition is a stroke.

53. A magnetic stimulator for non-invasively inducing electrical fields in a body part of a subject, comprising:
   means for producing stimulating currents that are complementary to an external surface of the body part and oriented in substantially a single direction; and
   means for conducting return path currents associated with the stimulating currents away from the external surface of the body part so that the electrical effects of the return path currents on the body part are reduced.

54. The magnetic stimulator of claim 53, wherein the stimulating currents flow through substantially parallel and spaced apart conductive elements in a base portion of the magnetic stimulator.

55. The magnetic stimulator of claim 53, wherein the return path currents flow through conductive elements of the magnetic stimulator that extend away from the external surface of the body part.

56. An electrically conductive coil for placing externally of the skull of a subject and operable to induce currents within the brain of the subject, comprising:
   a base portion, the base portion configured to provide a flow of electricity, thus producing a magnetic field in a region of the brain; and
   an extension portion for providing a return path for the flow of electricity through the base, the extension portion configured to place electrical currents flowing through the return path away from the region of the brain having the produced magnetic field,
   wherein the base portion comprises multiple substantially parallel and spaced apart stimulating elements configured to conduct electrical current in substantially a single direction of current flow, thereby inducing electrical fields within the region of the brain.

57. The electrically conductive coil of claim 56, wherein the extension portion comprises multiple return elements for respective return paths for the current in the stimulating elements.

58. The electrically conductive coil of claim 57, wherein the multiple return elements are spaced from the stimulating elements so that the electrical effect of the return path current on the body part is reduced.

59. The magnetic stimulator of claim 56, further comprising a power supply electrically connected to the coil.

60. The magnetic stimulator of claim 56, wherein the coil comprises a plurality of windings.

61. A magnetic stimulator for placing externally of the cranium of a subject and operable to induce currents within the body, comprising:
   an electrically conductive coil comprising a base portion and an extension portion, the base portion having a width axis and a length axis, and a concave first side configured to be complementary to the cranium of a subject, the extension portion projecting outwardly from the base portion, the coil in the base portion comprising elements spaced apart and transverse to the length axis such that the flow of current in these elements is in substantially the same direction; and a shield at least partially enclosing the extension portion.

62. The magnetic stimulator of claim 61, wherein the base portion is a partially toroidal or ovate base and is substantially arcuate along its length axis and is substantially arcuate along its width axis.

63. The magnetic stimulator of claim 62, wherein the base portion has an arch length along the length axis from 10 to 50 centimeters.

64. The magnetic stimulator of claim 62, wherein the base portion has an arch length along the width axis in a range from 2 to 15 centimeters.

65. The magnetic stimulator of claim 61, wherein the base portion comprises plural longitudinally-extending laterally spaced frame members.

66. The magnetic stimulator of claim 65, wherein at least two of the longitudinally-extending laterally spaced frame members are in a substantially non-parallel orientation.

67. The magnetic stimulator of claim 61, wherein the extension portion is positioned off-center relative to the base portion.

68. A magnetic stimulator for placing externally of the cranium of a subject and operable to induce currents within the body, comprising:

an electrically conductive coil comprising a base portion and an extension portion, the base portion having a width axis and a length axis, and a concave first side configured to be complementary to the cranium of a subject, the extension portion projecting outwardly from the base portion, the coil in the base portion comprising elements spaced apart and transverse to the length axis such that the flow of current in these elements is in substantially the same direction; and a cushion coupled to the base portion.

69. The magnetic stimulator of claim 68, wherein the transverse elements are arcuate.

70. A method for magnetically stimulating a region of the brain of a subject, the method comprising:

providing at least one current pulse through a plurality of stimulating pathways that are spaced apart from one another and configured to orient electrical current in a first direction, the stimulating pathways being complementary to the outer surface of the cranium of the subject and adjacent to the region of the brain being stimulated; and positioning electrical current that flows in a second direction opposite to the first direction away from the stimulating pathways so that the electrical effect of the current flowing in the second direction on the region of the brain being stimulated is reduced, wherein the electrical current flowing in the second direction flows through pathways that are removed from the surface of the cranium of the subject.

71. The method of claim 70, further comprising providing a first pulse of electrical current through a first subset of the stimulating pathways at a first time and providing a second pulse of electrical current through a second subset of the stimulating pathways at a second time after the first time.

* * * * *

UNITED STATES PATENT AND TRADEMARK OFFICE
CERTIFICATE OF CORRECTION

PATENT NO.        : 7,407,478 B2
APPLICATION NO.   : 10/399559
DATED             : August 5, 2008
INVENTOR(S)       : Zangen et al.

It is certified that error appears in the above-identified patent and that said Letters Patent is hereby corrected as shown below:

Column 1, line 43, "FIG. 8's" should read --figure-8's--.

Claim 22 Column 23, line 9, "configuTed" should read --configured--.

Claim 48 Column 25, lines 40 and 42, "return pathways" should read --return current pathways--.

Signed and Sealed this

Twenty-seventh Day of April, 2010

David J. Kappos
*Director of the United States Patent and Trademark Office*